(12) United States Patent
Vogt

(10) Patent No.: US 9,861,770 B2
(45) Date of Patent: Jan. 9, 2018

(54) VACUUM MOTOR FOR OPERATION OF A LAVAGE SYSTEM

(71) Applicant: Heraeus Medical GmbH, Wehrheim (DE)

(72) Inventor: Sebastian Vogt, Erfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 422 days.

(21) Appl. No.: 14/629,649

(22) Filed: Feb. 24, 2015

(65) Prior Publication Data

US 2015/0238710 A1  Aug. 27, 2015

(30) Foreign Application Priority Data

Feb. 24, 2014  (DE) .................. 10 2014 203 246

(51) Int. Cl.
  *F04B 9/12* (2006.01)
  *A61M 11/00* (2006.01)
  (Continued)

(52) U.S. Cl.
  CPC ....... *A61M 11/007* (2014.02); *A61C 17/0202* (2013.01); *A61C 17/028* (2013.01);
  (Continued)

(58) Field of Classification Search
  CPC ... A61M 11/007; A61M 11/02; A61M 3/0254
  See application file for complete search history.

(56) References Cited

U.S. PATENT DOCUMENTS

| | | |
|---|---|---|
| 4,278,078 A | 7/1981 | Smith et al. |
| 4,583,531 A | 4/1986 | Mattchen |
| (Continued) | | |

FOREIGN PATENT DOCUMENTS

| | | |
|---|---|---|
| DE | 3724110 A1 | 2/1989 |
| JP | H01267371 A | 10/1989 |
| (Continued) | | |

OTHER PUBLICATIONS

Australian Office Action for corresponding Australian Application No. 2015200809 dated Aug. 22, 2016.

(Continued)

*Primary Examiner* — Thomas E Lazo
(74) *Attorney, Agent, or Firm* — Norris McLaughlin & Marcus, P.A.

(57) ABSTRACT

A vacuum motor comprising a working plunger, an internal space, in which the working plunger is arranged such that it is mobile in linear direction, a resetting element that exerts, at least for part of the time, a force on the working plunger that acts in the direction of a front side of the internal space, a gas inlet opening for supplying ambient air or a compressed gas into the internal space, and a gas outlet opening for discharging the gas from the internal space. The gas outlet opening is connectable to a negative pressure source, whereby a control plunger is arranged between the working plunger and a rear side of the internal space such as to be mobile in linear direction in the internal space. The control plunger is supported as in a bearing such as to be mobile with respect to the working plunger, and a catch element and/or a spacer is arranged on said working plunger and/or control plunger, whereby the catch element, upon a motion of the working plunger towards the front side of the internal space, transfers the control plunger into the first position, and whereby the catch element or the spacer, upon a motion of the working plunger towards the rear side of the internal space, transfers the control plunger into the second position.

19 Claims, 11 Drawing Sheets

Figure 1:
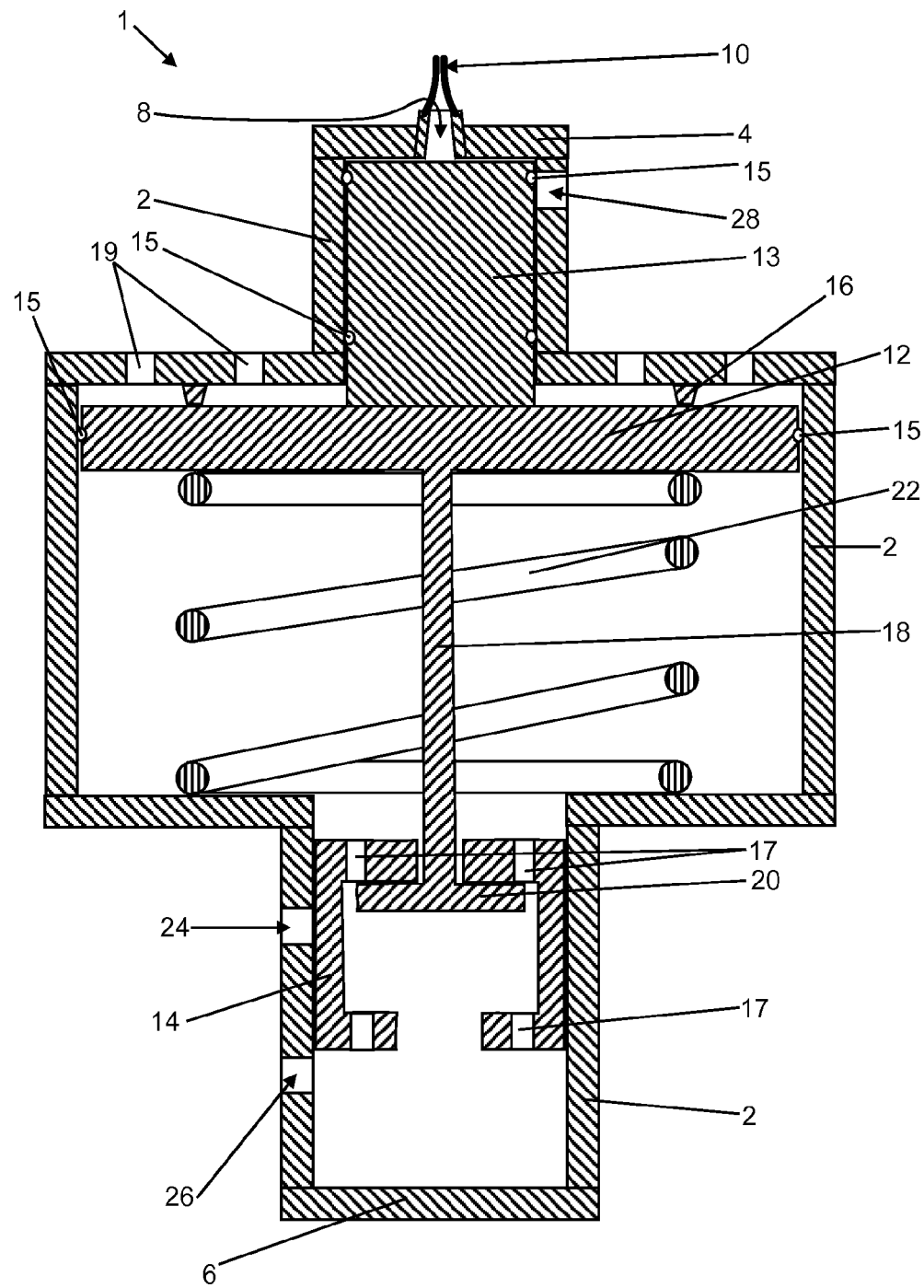

(51) Int. Cl.
  *A61C 17/028*  (2006.01)
  *A61M 3/02*  (2006.01)
  *A61M 11/02*  (2006.01)
  *F04B 9/127*  (2006.01)
  *F01B 29/02*  (2006.01)
  *A61C 17/02*  (2006.01)

(52) U.S. Cl.
  CPC ........ *A61M 3/0254* (2013.01); *A61M 3/0258* (2013.01); *A61M 11/02* (2013.01); *F01B 29/02* (2013.01); *F04B 9/127* (2013.01); *F04B 9/1215* (2013.01)

(56) References Cited

U.S. PATENT DOCUMENTS

| | | | |
|---|---|---|---|
| 4,993,924 A | | 2/1991 | Mukumoto et al. |
| 5,542,918 A | | 8/1996 | Atkinson |
| 5,554,011 A | * | 9/1996 | Bales ................. F01L 23/00 417/399 |
| 8,210,167 B2 | * | 7/2012 | Corbacho ......... A61M 15/0028 128/200.21 |
| 9,593,578 B2 | * | 3/2017 | Vogt .................... A61M 1/0064 |
| 2005/0084395 A1 | * | 4/2005 | Kang ..................... F04B 9/135 417/392 |
| 2013/0180396 A1 | | 7/2013 | Vogt et al. |

FOREIGN PATENT DOCUMENTS

| | | |
|---|---|---|
| WO | 8900461 A1 | 1/1989 |
| WO | 2012038003 A1 | 3/2012 |

OTHER PUBLICATIONS

Chinese Office Action for corresponding Chinese Application No. 201510087355.3 dated Dec. 16, 2016.

Sherman, et al., "The Role of Lavage in Preventing Hemodynamic and Blood-Gas Changes During Cemented Arthroplasty," The Journal of Bone and Joint Surgery, Incorporated; 1983, vol. 65-A, pp. 500-506, Canada.

Breusch, et al., "Zementierte Hüftendoprothetik—Verminderung des Fettembolierisikos mittels gepulster Druckspülung"; Orthopädie, 2000, vol. 29, pp. 578-586, Heidelberg, Germany. English Abstract on p. 579.

Breusch, et al., "Lavage Technique in Total Hip Arthroplasty, Jet Lavage Produces Better Cement Penetration Than Syringe-Lavage in the Proximal Femur"; The Journal of Arthroplasty; 2000, pp. 921-927, vol. 15, No. 7; Churchill Livingstone; Heidelberg, Germany.

Byrick, et al., "High-volume, High-Pressure Pulsatile Lavage During Cemented Arthroplasty," The Journal of Bone and Joint Bone Joint Surgery, Incorporated; 1989, pp. 1331-1336, Canada.

Christie, et al., "Medullary Lavage Reduces Embolic Phenomena and Cardiopulmonary Changes During Cemented Hemiarthroplasty," British Editorial Society of Bone and Joint Surgery; 1995, vol. 77-B, pp. 456-459, United Kingdom.

* cited by examiner

VACUUM MOTOR FOR OPERATION OF A LAVAGE SYSTEM

The invention relates to a vacuum motor comprising a working plunger and an internal space, in which the working plunger is arranged such as to be mobile in linear direction. The invention also relates to a lavage system comprising a vacuum motor of said type.

Moreover, the invention relates to the use of a vacuum motor of said type and to a method for generating a periodical motion by means of a vacuum or a negative pressure, and to a method for generating a spray puff by means of a method of said type.

Accordingly, the object of the invention is a simplified vacuum motor that can essentially be made from inexpensive plastic materials and is intended to drive devices that are operated only once, for a short period of time, in particular medical rinsing devices for single use made of plastic materials. Moreover, a pump for liquids that is driven by said vacuum motor is described. Moreover, the use of the vacuum motor to drive a pump for dispensing a rinsing fluid of a medical rinsing device (i.e. a lavage system) intended for single use only is proposed.

Medical rinsing systems are used widely in surgery to clean tissue areas. Said rinsing systems are called lavage systems. The lavage systems and rinsing liquids are used to produce spray jets that impinge on the tissue areas to be cleaned and exert a mechanical cleaning effect on said tissue areas. Specifically during the implantation of articular endoprostheses and during septic revisions, lavage systems have essential significance (R. M. Sherman et al.: The role of lavage in preventing hemodynamic and blood-gas changes during cemented arthroplasty. J. Bone Joint. Surg. 1983; 65-A: 500-506; S. J. Breusch et al.: Zementierte Hüftendoprothetik: Verminderung des Fettembolierisikos in der zementierten Hüftendoprothetik mittels gepulster Druckspülung. Orthopadie 2000; 29: 578-586; S. J. Breusch et al.: Lavage technique in THA: Jet-lavage Produces Better Cement Penetration Than Syringe-Lavage in the Proximal Femur. J. Arthroplasty. 200; 15(7): 921-927; R. J. Byrick et al.: High-volume, high pressure pulsatile lavage during cemented arthroplasty. J. Bone Joint Surg. 1989; 81-A: 1331-1336; J. Christie et al.: Medullary lavage reduces embolic phenomena and cardiopulmonary changes during cemented hemiarthroplasty. J. Bone Joint Surg. 1995; 77-B: 456-459).

Pulsed lavage systems have been known for a long time, for example from U.S. Pat. No. 4,583,531 A, U.S. Pat. No. 4,278,078 A, and U.S. Pat. No. 5,542,918 A. The lavage systems currently on the market are driven by means of electrical motors (for example InterPulse® Jet lavage made by Stryker GmbH & Co. KG) or compressed air (for example PALAVAGE® made by Heraeus Medical GmbH). Hand-held, electrically-driven lavage systems have also proven useful. However, a large battery block or rechargeable battery block, which only has a limited charge capacity due to its nature, always needs to be taken along. Battery blocks and rechargeable battery blocks are viewed critically in terms of their environmental impact. Compressed gas-driven lavage systems are advantageous in that compressed air is usually available in the operating theatre in unlimited quantities and thus allows rinsing liquid to be sprayed for any desired time without the energy supply being limited.

However, using compressed air-driven lavage systems requires the use of a two-tube system, in which the non-sterile compressed air is supplied through one tube and a second tube is used to discharge the non-sterile air, which is partially expanded after it drives the compressed air motor. However, systems driven by compressed air or any other compressed gas usually utilise a compressed gas motor as the drive. Most compressed gas motors for lavage systems are lamellar compressed gas motors. The compressed gas motor generates a rotary motion which is then translated into an oscillating linear motion. The oscillating linear motion is utilised to convey momentum to small volumes of a rinsing medium. It is common in this context to arrange at least one membrane between the drive and the inlet of rinsing liquid in order to be able to transmit the pulses to the rinsing liquid. This generates spray puffs at high pulse rates of 2,000 to 3,000 pulses per minute. This means that the compressed gas motor needs to be manufactured at high precision in order to tolerate such high rotation rates. Moreover, sufficiently stable storage must be available. For these reasons, the compressed gas motor is the most expensive component of common compressed air-driven lavage systems. Therefore, the compressed gas motor is generally arranged in a handle made of metal or other durable materials such that this component can be used multiply after appropriate reprocessing and sterilisation. Compressed gas motors utilise the pressure difference between the compressed gas used to drive the motor and the pressure of the ambient atmosphere.

A compressed gas motor is known from WO 2012/038003 A1. The compressed gas motor described in this reference has a two-part plunger with an intervening space and a passage through one of the plungers. This makes the structure of the motor particularly easy and inexpensive.

Numerous surgeries necessitate the aspiration of exudate and blood. Aspiration devices operated by negative pressure are used to aspirate said fluids. To operate these devices, most operating theatres (ORs) are equipped with stationary vacuum systems, which usually supply a negative pressure of 0.8 to 0.9 bar. Aside from these devices, mobile vacuum systems and/or negative pressure-generating systems are also used broadly.

But there is always a desire to have a motor of a less expensive design. Moreover, there is also a need to provide a motor that can be operated at a higher frequency and/or larger force.

But vacuum motors of this type are well-suited not only for lavage systems, but can also be used in all applications, in which a vacuum or a negative pressure source is available and an inexpensive drive is advantageous. Said requirements are evident, for example, in shaker facilities, in which bulk goods or powder need(s) to be transported, filled into containers and/or dosed. Likewise, said compressed gas motors can be used to advantage as pumps providing lubricants.

Accordingly, it is the object of the invention to overcome the disadvantages of the prior art. Specifically, the object is to discover an inexpensive and reliable vacuum motor that can be used for the afore-mentioned purposes. It is an object of the invention to develop a maximally-simplified plunger-equipped vacuum motor that can generate a periodical linear plunger motion. It shall be feasible to operate the vacuum motor with the vacuum provided by the customary stationary vacuum systems that are customary in surgical theatres for aspirating exudate and blood as well as with mobile aspiration systems. Moreover, a method for generating a linear periodical motion is to be developed, in which the vacuum motor to be developed is to be used or at least usable. It is important in this context that the vacuum motor works without needing complex costly valve systems and is simplified to the extent that the components of the vacuum motor can be produced inexpensively through injection moulding of plastic materials. The vacuum motor shall be usable to drive a medical rinsing device. Valve systems that take up a large volume and need to be positioned separately from the vacuum motor need to be avoided. Accordingly, the requisite valve functions shall be integrated into the vacuum motor in the most space-saving manner in order to enable the use of the vacuum motor as a drive in hand-pieces of lavage systems. Ideally, the time control of the valve functions should be implemented appropriately such that there is no "dead centre" at any point of the plunger motion. Moreover, a simplified pump for integration into hand-held lavage systems is to be developed along with the vacuum motor. A pump driven by the vacuum motor shall be simplified appropriately such that it can be produced inexpensively enough to allow it to be used in lavage systems intended for single use only.

The objects of the invention are met by a vacuum motor comprising a working plunger, an internal space, in which the working plunger is arranged such that it is mobile in linear direction, a resetting element that exerts, at least for part of the time, a force on the working plunger that acts in the direction of a front side of the internal space, a gas inlet opening for supplying ambient air or a compressed gas into the internal space, and a gas outlet opening for discharging the gas from the internal space, whereby the gas outlet opening is connectable to a negative pressure source, whereby a control plunger is arranged between the working plunger and a rear side of the internal space such as to be mobile in linear direction in the internal space, whereby the control plunger, in a first position, does not cover the gas outlet opening and covers the gas inlet opening and, in a second position, does not cover the gas inlet opening and covers the gas outlet opening, the control plunger is supported as in a bearing such as to be mobile with respect to the working plunger, and a catch element and/or a spacer is arranged on said working plunger and/or control plunger, whereby the catch element, upon a motion of the working plunger towards the front side of the internal space, transfers the control plunger into the first position, and whereby the catch element or the spacer, upon a motion of the working plunger towards the rear side of the internal space, transfers the control plunger into the second position.

In the scope of the present invention, a vacuum motor shall be understood to be a motor that can perform work by means of a pressure difference between a gas that is at a negative pressure and a gas at a higher pressure. In this context, a gas that is at atmospheric pressure, normal pressure or a higher pressure is used as working medium, preferably air from the surroundings of the vacuum motor, and the gas or the air is guided through the vacuum motor by means of the vacuum and/or negative pressure. The flow of the gas, preferably of the air, through the vacuum motor puts the working plunger into a periodical motion. A negative pressure is present already if the ambient pressure is higher than the negative pressure. A pressure difference of 100 hPa can be sufficient in an extreme scenario. It is preferred, according to the invention, for the pressure difference of the source of negative pressure to be 500 hPa or more and/or its absolute pressure to be 500 hPa or less.

Preferably, the resetting element exerts a force on the working plunger in the direction of the front side of the internal space in any position of the working plunger.

In a vacuum motor that is set up appropriately in vertical direction (front side of the vacuum motor down, in the direction of the ground), it is even feasible to forego a physical resetting element, since the working plunger can be restored by gravity in this case. Accordingly, the invention can provide the resetting element to be formed by setting-up the vacuum motor vertically by means of which the working plunger is accelerated towards the front side by means of gravity. The vacuum motor then has a particularly simple structure. However, it is preferred to have a physical resetting element present in order to be able to exert a stronger force on the working plunger and to render the function of the vacuum motor independent of the orientation with respect to the surface of the earth.

Preferably, the catch element is connected to the working plunger (or working cylinder) by means of a rod or a catch pin. Particularly preferably, the catch pin, or the rod as the case may be, the catch, and the working plunger are provided to be the same part.

The control plunger, the gas inlet opening, and the gas outlet opening form a valve element, whereby the gas inlet opening and the gas outlet opening are opened and closed repeatedly through the motion of the control plunger.

The invention proposes the internal space between the working plunger and the rear side to be closed except for the gas inlet opening and the gas outlet opening.

More specifically, the invention can provide the internal space between the working plunger in its position, in which it is moved maximally in the direction of the front side of the internal space, and the rear side of the internal space to be closed except for the gas inlet opening and the gas outlet opening.

The invention can provide the catch element, upon a motion of the working plunger away from the control plunger, to pull the control plunger along in the direction of the working plunger and to transfer the control plunger into the first position, and the catch element and/or the spacer, upon a motion of the working plunger towards the control plunger, to push the control plunger in the direction of the rear side and to transfer the control plunger into the second position.

Preferably, vacuum motors according to the invention are provided to have the working plunger and the control plunger be linearly mobile along the same axis. Preferably, the invention can provide the working plunger and the control plunger to be linearly mobile in the direction of the front side and in the direction of the rear side of the internal space in this context.

Moreover, in a vacuum motor according to the invention, the invention can provide the control plunger, in a third position between the first position and the second position, to cover both the gas inlet opening and the gas outlet opening.

This ensures that the vacuum motor does not stop in an intermediate position, in which the gas inlet opening and the gas outlet opening are open at the same time, and stays arrested due to this "short-circuiting". The inertia of the working plunger and/or the force of the resetting element make sure that these two openings do not stay closed permanently.

The invention can just as well provide at least one spacer to be arranged on the side of the control plunger that faces the working plunger and/or at least one spacer to be arranged on the side of the working plunger facing the control plunger or on the catch, in particular on the catch pin, such that an intervening space arises between the working plunger and the control plunger when these touch against each other. In this context, a refinement of the present invention can provide the gas inlet opening, in the second position, to open into said intervening space, whereby, when the working plunger and the control plunger touch against each other, the at least one spacer establishes a second distance between the working plunger and the control plunger that is smaller than a first distance that is established through the catch element.

The spacer can be formed by means of a tube along the central axis of the internal space through which the catch and/or the catch pin or the rod, on which the catch is fastened to the working plunger or to the control plunger, extends. Alternatively, the at least one spacer can just as well be provided as a pin. Preferably, the spacer or spacers and the working plunger or control plunger are provided to be the same part.

It is essential to the invention that the distance between the working plunger and the control plunger enlarges when the resetting element accelerates the working plunger in the direction away from the rear side. As a result, an impact or a major force can be applied via the catch element to accelerate the control plunger such that the vacuum motor cannot come to a standstill due to a resting or blocked control plunger. For the same purpose, the invention can provide the mass of the working plunger, and in particular of the working plunger with the catch element firmly connected to it, to be larger than the mass of the control plunger.

Moreover, the invention can provide the resetting element to be an elastic compression spring that is arranged in the internal space between the working plunger and the rear side of the internal space.

This provides a vacuum motor that is particularly simple and inexpensive to manufacture and works well regardless of its orientation. Moreover, the frequency of the motor can be set through selection of the spring constant.

In this context, the spring can be provided to touch against the working plunger. However, it is preferred not to have the spring touch against the rear side of the internal space. Rather, the spring touches against a support surface that is arranged between the rear side of the internal space and the working plunger, preferably is arranged between the control plunger and the working plunger. The support surface can be provided by a limiting wall of a middle or front part of the internal space, in which the working plunger moves. According to the invention, the spring preferably has a spring constant between 1 N/cm and 100 N/cm. Preferably, the elastic compression spring is a coil spring or a leaf spring.

In order to be able to position the vacuum motor variably with respect to the surface of the earth, as may be required in the case of hand-held lavage systems and/or to be able to exert a larger moment on the working plunger, the invention can preferably provide the resetting element to be a physical resetting element, in particular an elastic spring, such as, for example, a steel spring and/or a gas-operated spring system. Theoretically, the elastic spring can just as well be a tension spring. As a tension spring, the elastic spring is arranged in the internal space between the front side of the internal space and the working plunger. For this purpose, the tension spring needs to be anchored both on the front side of the internal space and on the working plunger. A compression spring is preferred though. As a compression spring, the elastic spring is arranged in the internal space between the working plunger and the rear side of the internal space.

Moreover, the invention proposes the control plunger, in the first position, to be pulled via the catch element in the direction of the front side by the resetting element, whereby the gas outlet opening opens into the intervening space between the control plunger and the rear side of the internal space.

This design allows the vacuum motor to be brought into a starting position (the starting position of the working plunger and control plunger), from which it starts when a gas is drawn out through the gas outlet opening, in a situation, in which no gas is drawn through the gas outlet opening out of the internal space.

The invention can just as well provide at least one gas-permeable passage to be arranged in the control plunger and to connect the front side of the control plunger facing the working plunger to the rear side of the control plunger facing the rear side of the internal space.

The control plunger can then touch against the internal walls of the internal space by its entire circumference. This ensures a stable linear guidance of the control plunger in the internal space.

According to a preferred embodiment, the invention can provide the working plunger to touch against the internal wall of the internal space by its entire circumference, preferably to touch by its entire circumference in gas-tight and pressure-tight manner against the internal space by means of a sealing element.

Accordingly, according to the invention, the working plunger can preferably be supported as in a bearing tightly against the internal walls of the internal space. This ensures that the compressed gas does not flow past the working plunger to the effect that the performance or power of the vacuum motor is reduced.

For vacuum motors according to the invention for producing a mechanical motion, the invention can preferably provide a rod, in particular a plunger rod, to be attached to the side of the working plunger that faces away from the control plunger and projects from the internal space, preferably projects through the front side of the internal space.

In this variant, the rod produces a periodical thrust. Through the use of a plunger rod that is connected to the working plunger by means of an axle, the periodical motion of the working plunger can be converted into a rotary motion. For this purpose, the plunger rod preferably is or can be connected to a crankshaft.

Preferred embodiments of the invention can also be characterised in that an ejection opening is provided in the front side of the internal space opposite from the rear side, and a liquid supply opening is arranged in the front side and/or in the lateral wall of the internal space and the opening is not covered by the working plunger or a pump plunger, at least for part of the time, and, in the non-covered state, is arranged between the working plunger or the pump plunger and the front side of the internal space.

Due to this design, the swept volume of the working plunger is used, at least in part, to take up liquid and/or to take up a mixture of gas and liquid. When the working plunger is being moved in the direction of the front side of the internal space, the liquid and/or the liquid-gas mixture is ejected through the ejection opening. The vacuum motor can then be used directly for lavage systems.

In this context, the invention can provide the ejection opening to be connected to the surroundings through a valve element, in particular a lip valve, whereby the valve element is open in the presence of sufficient over-pressure as compared to the ambient pressure and is closed otherwise, and can provide a tube or a hose with a non-return valve to be connected to the liquid supply opening and to open in the presence of an under-pressure in the internal space between the working plunger or the pump plunger and the front side of the internal space and to thus enable liquid to be supplied into the internal space.

This allows the internal space to be filled automatically with a liquid. As a result, a particularly simple and inexpensive design of a vacuum motor for a lavage system is attained. With regard to the definition of a sufficient pressure, reference shall be made to known lip valves for the same or similar purposes.

Moreover, said vacuum motors can be provided appropriately such that the working plunger comprises, on the side facing the front side, a pump plunger that has an at least 50% smaller cross-sectional surface area than the part of the working plunger facing the rear side, whereby the cross-section of the internal space is adapted to the cross-section of the pump plunger and to the cross-section of the working plunger.

This ensures that the part of the working plunger facing the rear side is mobile in the internal space and that the pump plunger can periodically open and close the liquid supply opening by means of the motion of the working plunger and thus facilitates periodical ejection of liquid from the ejection opening.

It is preferred according to the invention for the cross-sectional surface area of the pump plunger to be 75% smaller than that of the working plunger. Accordingly, the diameter is 50% smaller provided the geometry of the pump plunger and the working plunger is cylindrical.

Vacuum motors according to the invention can also be provided such that the catch element is a string, a cable, a thread, a chain or an elastic spring that is attached to the working plunger and to the control plunger or the catch element comprises a rod, a string, a cable, a thread, a chain or an elastic spring that is attached to the working plunger or to the control plunger and has a catch attached to it that engages a projection in the working plunger or in the control plunger during the periodical motion of the working plunger, whereby the catch element preferably is provided by a rod that is attached to the working plunger and extends through a feed-through in the control plunger and has the catch attached to it that does not fit through the feed-through in the control plunger and engages the feed-through on the rear side of the feed-through of the control plunger in order to pull the control plunger along, when the working plunger is sufficiently far away from the control plunger for this purpose and moves in the direction away from the control plunger.

Said catch elements can be used to attain an increase in the distance between the working plunger and the control plunger in structurally simple manner before the control plunger is being pulled along by the working plunger. By this means, the efficiency of the motor can be improved and the risk of a standstill of the motor can be decreased.

The invention can preferably provide the catch to hit against an opposite limit stop in the working plunger or in the control plunger, whereby the catch hits against the limit stop in the interior of the control plunger when the working plunger moves in the direction of the control plunger and is positioned close enough to the control plunger.

Preferred refinements of the invention can just as well provide the internal space, at least regions thereof, to be cylindrical or to be cylindrical in the region of a working space of the working plunger or in the entire swept volume of the working plunger and control plunger.

The cylindrical internal space need not be completely cylindrical. It is sufficient that the swept volume of the working plunger is cylindrical. Preferably, the swept volume of the control plunger is cylindrical as well. The swept volume of the control plunger need not be cylindrical if cut-outs or other recesses are provided therein that serve to allow the gas or air to get past the control plunger into the space between the control plunger and the rear side of the internal space. The space between the maximal deflection of the working plunger in the direction of the front end of the internal space and the front end of the internal space need not necessarily be cylindrical, if no pump plunger is provided therein. However, the structure of the vacuum motor is simplified if this part of the internal space is cylindrical as well. A cylinder in the scope of the present invention and according to general definition is a body bounded by two parallel, planar, congruent surfaces (base surface and cover surface) and a jacket surface and/or cylinder surface, whereby the jacket surface is formed by parallel straight lines. This means that the cylinder is generated through shifting a planar surface along a straight line that is not positioned in said plane. The height of the cylinder is given by the distance between the two planes, in which base surface and cover surface are situated.

If the straight lines are perpendicular to base surface and cover surface, the structure is called a straight cylinder. The straight cylindrical geometry of the internal space is preferred according to the invention, but particularly preferably relates only to one or more partial region(s) of the entire internal space. A straight circular cylinder in the scope of the present invention is therefore only a special case of a cylindrical geometry.

The working plunger closes tightly against the internal walls in all positions such that the internal space is always separated into at least two separate chambers by the working plunger. Preferably, the internal space is separated into three separate chambers by the working plunger and the pump plunger. Preferably, said separation is gas-tight and pressure-tight.

The invention can provide the length of the control plunger in axial direction of the internal space to be at least equal to the sum of the axial distance of the gas inlet opening from the gas outlet opening and the axial cross-sections of the gas inlet opening and gas outlet opening. The axial cross-sections of the gas inlet opening and gas outlet opening are the cross-sections of the gas inlet opening and gas outlet opening in axial direction of the internal space.

Preferably, the linear motion of the working plunger and control plunger proceeds along a straight line that corresponds to the axis of symmetry of the cylindrical internal space.

According to a preferred variant, the present invention can provide the working plunger to comprise two differently-sized cross-sectional surfaces perpendicular to the linear motion direction of the working plunger, whereby the internal space comprises matching internal walls with different cross-sectional surfaces and the cross-sectional surface on the side of the working plunger facing the rear side is at least 100% larger than the cross-sectional surface of the opposite front side of the working plunger, preferably the cross-sectional surface on the side of the working plunger facing the rear side is at least four times the size of the cross-sectional surface of the opposite front side of the working plunger. Presently, the front part of the working plunger is referred to as the pump plunger in most cases.

This is advantageous since, if the part of the working plunger that faces the rear side and on which the gas flowing through the vacuum motor performs its work has the larger cross-sectional surface, a stronger force can act in order to tension a resetting element with a stronger resetting force which, in turn, leads to an increase in the working frequency of the vacuum motor.

The invention can preferably provide the part of the working plunger or working plungers facing the rear side to have a diameter of at least 4 cm.

Referring to oval or circular cross-sectional surfaces of the working plunger, it is always possible to refer to a radius, diameter or cross-section rather than a cross-sectional surface. Accordingly, referring to oval or circular cross-sectional surfaces of the working plunger or other cross-sectional surfaces of the working plunger to which a cross-section, radius or diameter is applicable, the invention can provide the working plunger to comprise two differently-sized diameters or cross-sections perpendicular to the motion direction of the working plunger, whereby the internal space comprises matching internal walls having different diameters or cross-sections and the diameter or cross-section on the side of the working plunger facing the rear side is larger than the diameter or cross-section of the opposite front side of the working plunger. In this context, the invention can preferably provide the diameter or cross-section on the side of the working plunger facing the rear side to be at least twice the diameter or cross-section of the opposite front side of the working plunger.

A refinement of the invention proposes a second resetting element to be arranged in the internal space, which exerts a force on the control plunger in the direction of the working plunger, at least for part of the time, while the vacuum motor is running, whereby preferably the second elastic resetting element is arranged between the control plunger and the rear side of the internal space, particularly preferably an elastic compression spring is arranged between the control plunger and the rear side of the internal space as second resetting element.

This allows the control plunger to be positioned appropriately such that the gas outlet opening is exposed, i.e. is not covered by the control plunger, when the vacuum motor is in its resting state.

Accordingly, the invention can provide the vacuum motor to be manufactured from thermoplastic materials with polypropylene, polyethylene, polyamide-6, and polyamide-12 being particularly preferred. In addition, all common plastic materials in this technology are well-suited.

Vacuum motors according to the invention preferably work at a frequency of 500 to 2,000 cycles per minute, particularly preferably at a frequency of 1,000 to 1,500 cycles per minute.

The objects of the invention with regard to a lavage system are met by a lavage system comprising at least one vacuum motor according to any one of the preceding claims, in which the vacuum motor or vacuum motors can be used to generate a periodical spray puff of a liquid.

The lavage system can be provided to comprise a connector for a negative pressure source and a manually-operable control valve, whereby the control valve is connected to the negative pressure source by means of a gas line, and the gas outlet opening of the vacuum motor is connected to the control valve by means of a gas line. The invention can preferably provide a liquid supply opening of the vacuum motor to be connected to a liquid line.

The objects of the invention are also met by the use of a vacuum motor according to the invention as motor for a lavage system, a rapping motor, a vibration motor, as drive for a dosing facility, as shaker motor or as pump, in particular as lubricant pump.

The underlying objects of the invention are also met by a method for generating a periodical motion using a vacuum or negative pressure, in particular through the use of a vacuum motor according to the invention, in which A) the working plunger and the control plunger, in a starting state, are situated in the internal space such as to be at a first distance from each other, whereby the control plunger closes the gas inlet opening and the gas outlet opening is open;

B) the gas between the working plunger and the control plunger and between the working plunger and the rear side of the internal space is drawn out of the internal space through the gas outlet opening;

C) the working plunger is accelerated and moved in the direction of the rear side of the internal space towards the control plunger by the pressure difference between the gas pressure exerting on the front side versus the gas pressure exerting on the rear side of the working plunger, whereby the distance between the working plunger and the control plunger decreases and the resetting element takes up and stores energy due to the motion of the working plunger;

D) the control plunger is pushed along by the working plunger by means of the catch element or a spacer, preferably as soon as a second distance is reached;

E) the control plunger closes the gas outlet opening due to the motion of the control plunger;

F) the control plunger opens the gas inlet opening due to the motion of the control plunger;

G) a compressed gas or ambient air flows through the gas inlet opening into the internal space, preferably flows through the gas inlet opening into the internal space between the working plunger and the control plunger;

H) the resetting element accelerates the working plunger in the direction of the front side of the internal space;

I) the control plunger is pulled along by the working plunger by means of the catch element and moves the same in the direction of the front side of the internal space, preferably as soon as a first distance is reached;

J) the gas inlet opening is closed again by the reverse motion of the control plunger; and K) the reverse motion of the control plunger opens the gas outlet opening again such that the gas between the working plunger and the rear side of the internal space is drawn out of the internal space again.

The steps proceed in logical and chronological order, whereby the periods of time, at which the steps according to the invention proceed, can overlap in part and in time. Preferably, the vacuum motor is restored to its starting state by the resetting element. However, the vacuum motor also works if the starting state is reached again only once no negative pressure is available any longer at the gas outlet opening.

Methods according to the invention can provide the cycle to repeat upon renewed evacuation of the gas situated in the internal space between the working plunger and the rear side of the internal space.

Moreover, the invention can provide the second distance between working plunger and control plunger to be set by means of at least one spacer and the first distance between working plunger and control plunger to be set by the catch element, preferably by means of the length of the catch element.

Preferably, the first distance is selected to be at least 1.5-fold the second distance.

Moreover, methods according to the invention can provide the periodical linear motion of the working plunger in the vacuum motor to be triggered independently, by the effect of vacuum or negative pressure without any action of external valves.

According to the invention, it is preferred that the vacuum or negative pressure corresponds to a negative pressure of at least 0.5 bar with respect to the ambient atmosphere.

Methods according to the invention are preferably repeated at a frequency of 500 to 2,000 cycles per minute, particularly preferably are repeated at a frequency of 1,000 to 1,500 cycles per minute.

The underlying objects of the invention are also met by a method for generating a spray puff comprising the aforementioned process steps according to the invention, whereby, upon a motion of the working plunger, in particular of a pump plunger of the working plunger, away from the rear side of the internal space, a rinsing liquid or a liquid-gas mixture is extruded from the space between the working plunger and the front side of the internal space through an ejection opening on the front side of the internal space, and, upon a motion of the working plunger, in particular of the pump plunger of the working plunger, towards the rear side of the internal space, a liquid or a liquid-gas mixture is pushed or drawn through a liquid supply opening into the space between the working plunger, in particular the pump plunger, and the front side of the internal space.

In this method, the invention can provide, upon the motion of the working plunger, in particular of the pump plunger, towards the front side of the internal space, the pressure in the space between the working plunger, in particular the pump plunger, and the front side of the internal space to open and/or keep open a valve at the ejection opening and to close and/or keep closed a non-return valve connected to the liquid supply opening, and, upon the motion of the working plunger, in particular of the pump plunger, towards the rear side of the internal space, the lesser pressure in the space between the working plunger, in particular the pump plunger, and the front side of the internal space to close and/or keep closed the valve on the ejection opening and to open and/or keep open the non-return valve connected to the liquid supply opening.

The invention is based on the surprising finding that having a working plunger and a control plunger with a variable distance from each other allows a simple and reliably running vacuum motor to be provided that has no dead centre at which the vacuum motor comes to a standstill without being able to re-start again. Said "dead centre" is prevented according to the invention in that a defined state of the valves, i.e. of the control plunger and the cover of the gas inlet opening and of the gas outlet opening, is feasible in the vacuum motor at all times by means of the control plunger. Defined state shall be understood to mean that a valve is either open or closed. Said defined state is ensured by the force on the working plunger that is generated by the resetting element. It can be ensured by appropriately setting the two distances of the two plungers (working plunger and control plunger) with respect to each other during operation of the vacuum motor that the vacuum motor can be utilised as appropriate for the respective purpose. In particular, using the vacuum motor as a pump for generating spray puffs of a rinsing liquid, the vacuum motor can be designed in simplest manner in that the swept volume of the working plunger is used directly as the pump, whereby preferably, the front part of the working plunger, which is also referred to as pump plunger in the scope of the invention and which has a smaller swept volume than the rear part of the working plunger, on which the gas performs work. The smaller swept volume is attained by means of a smaller cross-section perpendicular to the direction of motion, in particular to the cylinder axis of the working plunger.

The vacuum motor can utilise the negative pressure sources and/or vacuum sources that are present anyway in many areas, in particular in surgical theatres, to drive the vacuum motor and/or the working plunger. No additional energy source is then needed to drive the vacuum motor. Simultaneously, negative pressure and/or vacuum is available in virtually unlimited quantity in this setting.

The working plunger and the control plunger do not move concurrently while keeping a constant distance in this respect. The working plunger moves first. If the working plunger is situated at less than a certain distance from the control plunger and thus has attained a certain speed, the working plunger suddenly pushes the control plunger in the direction of the rear side of the internal space of the vacuum motor, in which the catch hits against the projection (second limit stop) of the control plunger or of the working plunger or the spacer of the working plunger hits against the control plunger or the spacer of the control plunger hits against the working plunger and thus, in all aforementioned cases, the control plunger is moved along. Accordingly, the rationale underlying the present invention, in particular, is to decouple, in time, the valve control by means of the control plunger from the motion of the working plunger. This surprisingly allows a forceful motion of the working plunger to be attained. A forceful motion of the working plunger of the vacuum motor according to the invention results also by comparison to the compressed gas motor according to WO 2012/038003 A1 having the two-part, but firmly connected working plunger, such that more force can be transmitted upon each motion of the working plunger.

This allows the front part of the internal space to be used as pump space directly and without a gear or a transmission for enhancement of the force. The spray puff or puff of rinsing liquid of a lavage system can thus be generated directly by means of the working plunger. This allows energy losses during the pumping process to be prevented. It is therefore excluded that the gear or a part of the transmission might become defective. Moreover, the structure becomes more compact and less expensive as compared to when these parts have to be attached or installed.

In this context, the invention is based on the following rationale and can be implemented as follows: A resetting element pushes an axially shiftable working plunger within a hollow cylinder having two or three regions differing in diameters against one side of the hollow cylinder or in the direction of one side of the hollow cylinder. A gas inlet opening and a gas outlet opening are arranged separate from each other in the jacket surface of the hollow cylinder and are connected to the internal space of the hollow cylinder in gas-permeable manner. The gas inlet opening is situated in the direction of the working plunger and resetting element and the gas outlet opening is situated opposite with respect to these in the direction of the gas-impermeable closure of the hollow cylinder. A control plunger and/or a valve element can be shifted in axial direction in the hollow cylinder and, depending on its position, can close either just the gas inlet opening, while the gas outlet opening is open at this time, or close just the gas outlet opening, while the gas inlet opening is open at this time.

The control plunger and/or the valve element possess a hollow space that extends axially through the control plunger and/or valve element. The front side of the working plunger, which is engaged by the resetting element, has a catch pin situated on it that has a catch arranged on its end. The catch pin is mobile in axial direction in the hollow space of the valve element. A first limit stop is arranged on the valve element in the direction of the front side of the working plunger, on which the catch pin is arranged, and a second limit stop is arranged on the other narrow side of the valve element. The catch can engage said second limit stop upon axial motion of the catch pin resulting from the motion of the working plunger in the direction of the resetting element, and move the valve element in opposite direction to the resetting element upon the axial motion. In the process, the gas outlet opening is being closed and the gas inlet opening is being opened. Upon the reverse motion of the working plunger resulting from the action of the resetting element, the catch hits against the first limit stop and shifts the valve element axially in the direction of the working plunger, whereby the gas inlet opening is being closed and the gas outlet opening is being opened.

Advantageously, the front side of the working plunger, which is opposite from the front side with the catch pin attached to it, has at least one spacer element and/or spacer arranged on it that places said front side of the working plunger at a distance from the wall of the hollow cylinder, thus forming a gap. This gap is required in order to prevent the working plunger from becoming suctioned to the hollow cylinder wall in undesirable manner.

The vacuum motor works such that, firstly, a vacuum is drawn through the opened gas outlet opening. The negative pressure pulls the working plunger against the resetting element. This is being tensioned in the process. Concurrently, the catch pin with the catch moves along within the valve element which is still being moved at this time. When, upon the working plunger moving further in the direction of the resetting element and thus of the catch pin within the valve element, the catch hits against the second limit stop, the valve element is shifted axially. Concurrently, the valve element is pushed over the gas outlet opening which closes it. Closed until this time by the valve element, the gas inlet opening is opened concurrently by the shifting of the valve element. Then, ambient air flows into the hollow cylinder. The negative pressure is being established. At this time, no or only little negative pressure acts on the working plunger. As a result, the resetting element expands and moves the working plunger back into its starting position, whereby the resetting element largely relaxes. If the working plunger moves axially opposite to the resetting element, the catch pin is also moved along in said direction. The catch then hits against the first limit stop and shifts the valve element again, whereby the gas inlet opening is being closed and the gas outlet opening is being opened. The process is then repeated for as long as a negative pressure is applied to the gas outlet opening. It is essential in this context that the motion of the valve element does not take place synchronous to the motion of the working plunger. Due to the inertia of the moving working plunger and catch pin, the valve element travels over the gas inlet opening and the gas outlet opening. Due to the inertia of the moving working plunger, the so-called "dead centre" is passed without needing flywheels or similar devices for this purpose.

As a result, the vacuum motor can start-up automatically, without any action of the vacuum, since the resetting element pushes the working plunger into the pre-determined starting position, in which the gas outlet opening is open and the gas inlet opening is being closed by the valve element. As a result, the vacuum motor can start-up automatically at any time since the vacuum and/or negative pressure can act on the working plunger when the gas outlet opening is open.

According to the invention, the control plunger arranged in the internal space such as to be mobile in linear direction is used as valve element.

For this purpose, a vacuum motor according to the invention can, for example, be composed of:

a) a hollow cylinder that comprises at least one gas outlet opening and one gas inlet opening arranged separately from each other on the jacket surface of the hollow cylinder;

b) a working plunger that is arranged in the hollow cylinder such as to be mobile in axial direction;

c) an elastic resetting element that is arranged in the hollow cylinder and engages on a front side of the working plunger;

d) a catch pin that is arranged on the front side of the working plunger, which is engaged by the resetting element;

e) a catch that is connected to the catch pin;

f) a control plunger that can be shifted in axial direction in the hollow cylinder and has a length in axial direction that is at least equal to the sum of the axial distance between the gas outlet opening and the gas inlet opening, whereby the control plunger, shifted axially over the gas outlet opening, closes the gas outlet opening in gas-tight manner and the gas inlet opening is open at the same time, the control plunger, shifted over the gas inlet opening, closes the gas inlet opening in gas-tight manner and the gas outlet opening is open at the same time;

g) the control plunger possesses at least one hollow space, in which the catch pin can be shifted in axial direction;

h) a first limit stop on the control plunger that is arranged appropriately on the side of the control plunger facing the working plunger such that the motion of the working plunger in the direction of the resetting element caused by relaxation of the resetting element moves the catch pin through the hollow space of the control plunger and then the catch arranged on the catch pin hits against the first limit stop and moves the control plunger in the same direction as the direction of expansion of the resetting element if the working plunger moves further;

i) a second limit stop on the control plunger that is arranged appropriately on the side of the control plunger facing away from the working plunger, such that a motion of the working plunger, caused by the action of vacuum with the resetting element concurrently being compressed, moves the catch pin through the hollow space of the control plunger and then the catch arranged on the catch pin hits against the second limit stop and moves the control plunger in the direction opposite to the direction of expansion of the resetting element if the working plunger moves further; and j) a gas-impermeable closure on the end of the hollow cylinder such that a hollow space is formed by the hollow cylinder that is bounded by the working plunger and the gas-impermeable closure and in which the catch pin, the catch, and the control plunger are situated.

A method according to the invention for generating a periodical linear motion by means of a vacuum motor according to the invention can be implemented, for example, in that a) firstly, the resetting element pushes the working plunger appropriately such that the valve element and/or the control plunger covers the gas inlet opening to close it and the gas outlet opening is open;

b) the action of negative pressure draws gas from the hollow space through the open gas outlet opening, whereby the working plunger is moved against the resetting element until the catch reaches the second limit stop;

c) then the catch engages the second limit stop of the control plunger and, upon further motion of the working plunger, shifts the control plunger axially, whereby the gas outlet opening is being closed by the control plunger and the gas inlet opening is being opened;

d) then air from the surrounding atmosphere flows through the open gas inlet opening until the residual negative pressure is so low that the resetting force of the resetting element exceeds the force of the residual negative pressure remaining in the hollow cylinder, whereby the resetting element pushes the working plunger in axial direction into the starting position, whereby the catch hits against the first limit stop and then moves the control plunger axially such that the control plunger covers the gas inlet opening to close it and opens the gas outlet opening; and e) the process of steps a-d is being repeated.

The process is repeated for as long as vacuum or negative pressure is connected to the hollow space and/or the internal space of the vacuum motor by means of the gas outlet opening.

Another exemplary embodiment of the invention is a negative pressure-driven liquid pump having a vacuum motor according to the invention, composed of a) a hollow cylinder;

b) a gas outlet opening in the hollow cylinder;

c) a gas inlet opening in the hollow cylinder, whereby the gas inlet opening is arranged to be separate from the gas outlet opening;

d) a liquid inlet opening in the hollow cylinder;

e) a liquid outlet opening in the hollow cylinder;

f) a working plunger that is arranged in the hollow cylinder such as to be mobile in axial direction and possesses a first front side and a second front side;

g) the hollow cylinder being closed on both front sides;

h) the hollow cylinder and the first front side of the working plunger forming a first hollow space A, whereby the liquid inlet opening and the liquid outlet opening as well connect the first hollow space to the liquid feed and the liquid drain;

i) an elastic resetting element that is arranged in the hollow cylinder and engages on a second front side of the working plunger;

j) a catch pin that is arranged on the second front side of the working plunger, which is engaged by the resetting element;

k) a catch that is connected to the catch pin;

l) a control plunger that can be shifted in axial direction in the hollow cylinder and has a length in axial direction that is at least equal to the sum of the axial distance between the gas outlet opening and the gas inlet opening, whereby the control plunger, shifted axially over the gas outlet opening, closes the gas outlet opening in gas-tight manner and the gas inlet opening is open at the same time, the control plunger, shifted over the gas inlet opening, closes the gas inlet opening in gas-tight manner and the gas outlet opening is open at the same time;

m) the control plunger possesses at least one hollow space, in which the catch pin can be shifted in axial direction;

n) a first limit stop on the control plunger that is arranged appropriately on the side of the control plunger facing the working plunger, such that the motion of the working plunger caused by relaxation of the resetting element moves the catch pin through the hollow space of the control plunger and then the catch arranged on the catch pin hits against the first limit stop, and the control plunger, upon the working plunger moving in the direction of expansion of the resetting element, is moved in the same direction; and o) a second limit stop on the control plunger that is arranged appropriately on the side of the control plunger facing away from the working plunger, such that the motion of the working plunger, caused by the action of a vacuum with the resetting element being compressed concurrently, moves the catch pin through the hollow space of the control plunger and then the catch arranged on the catch pin hits against the second limit stop, and moves the control plunger, upon the working plunger moving further, in the direction against the direction of expansion of the resetting element;

p) a gas-impermeable closure on the end of the hollow cylinder such that a hollow space is formed by the hollow cylinder that is bounded by the working plunger and the gas-impermeable closure and in which the catch pin, the catch, and the control plunger are situated.

Figure 2:
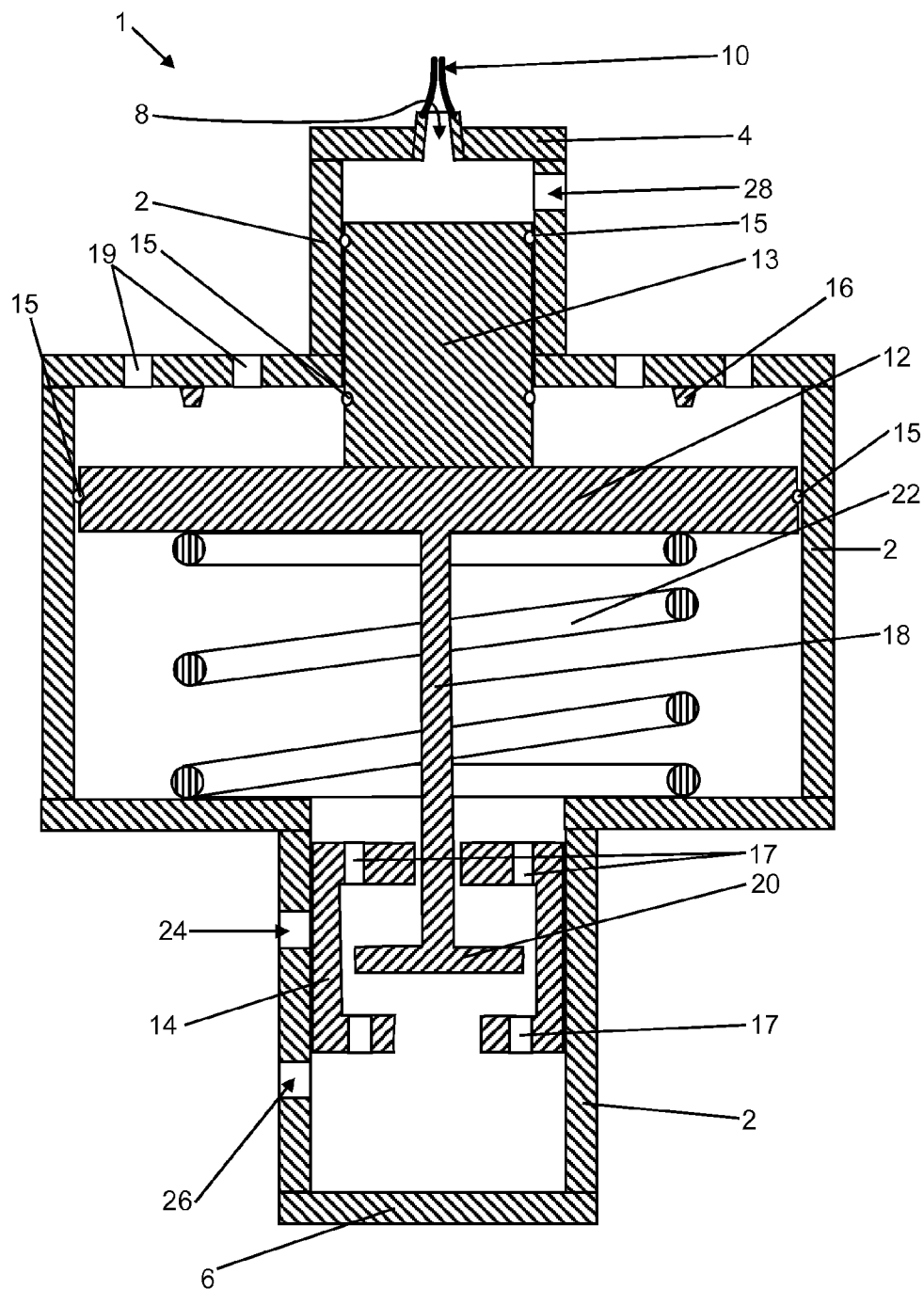
Figure 3:
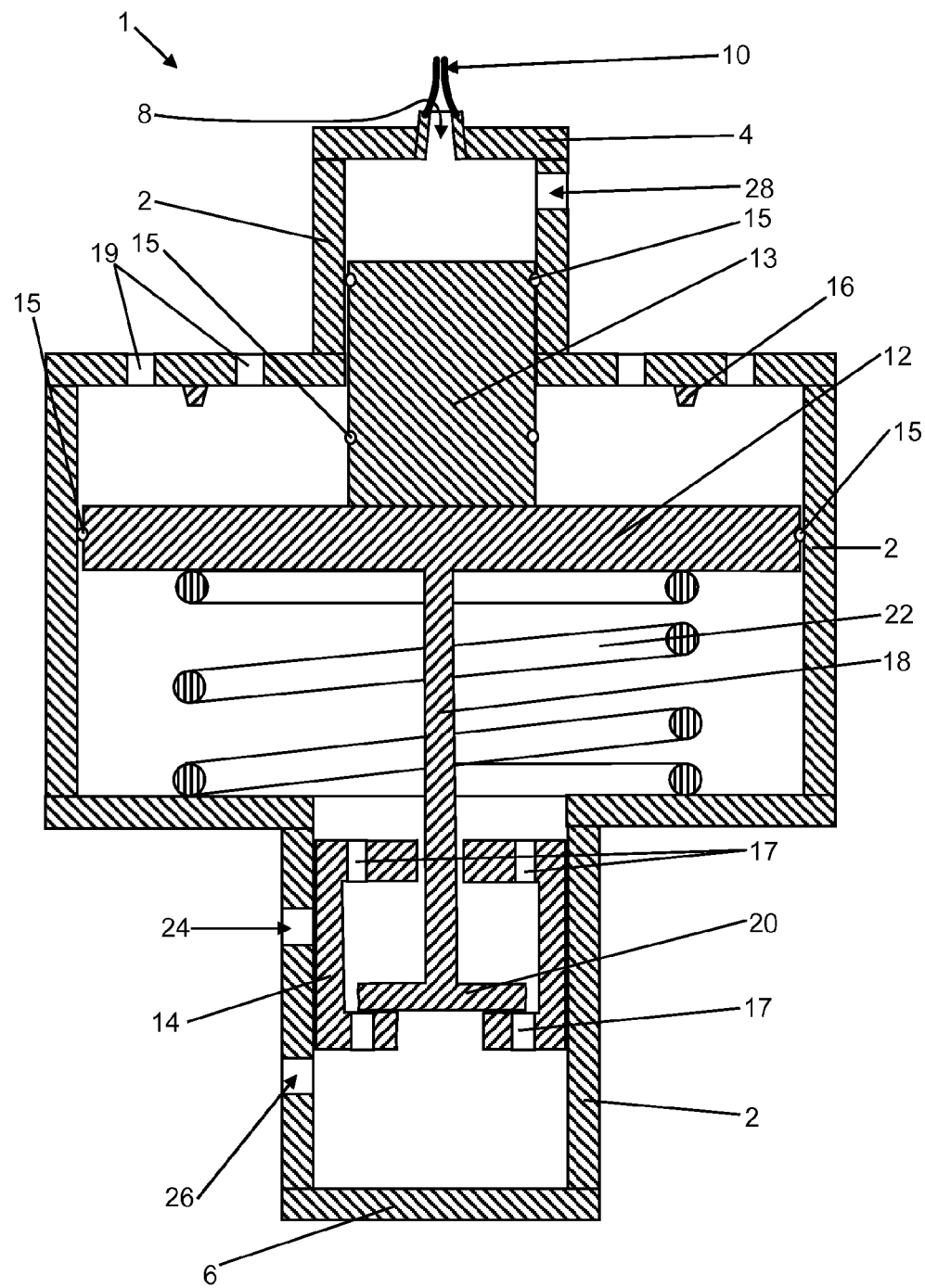
Figure 4:
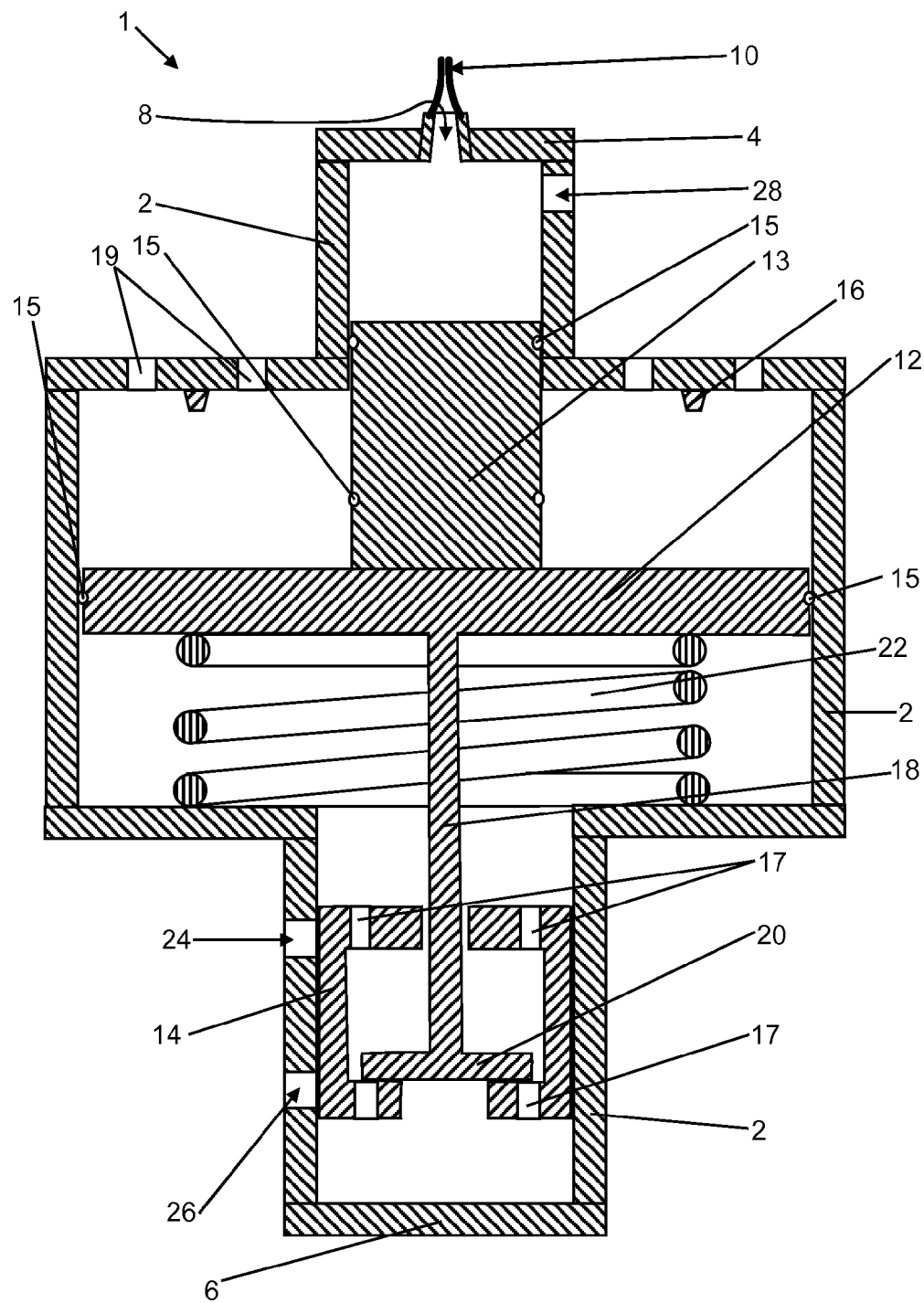
Figure 5:
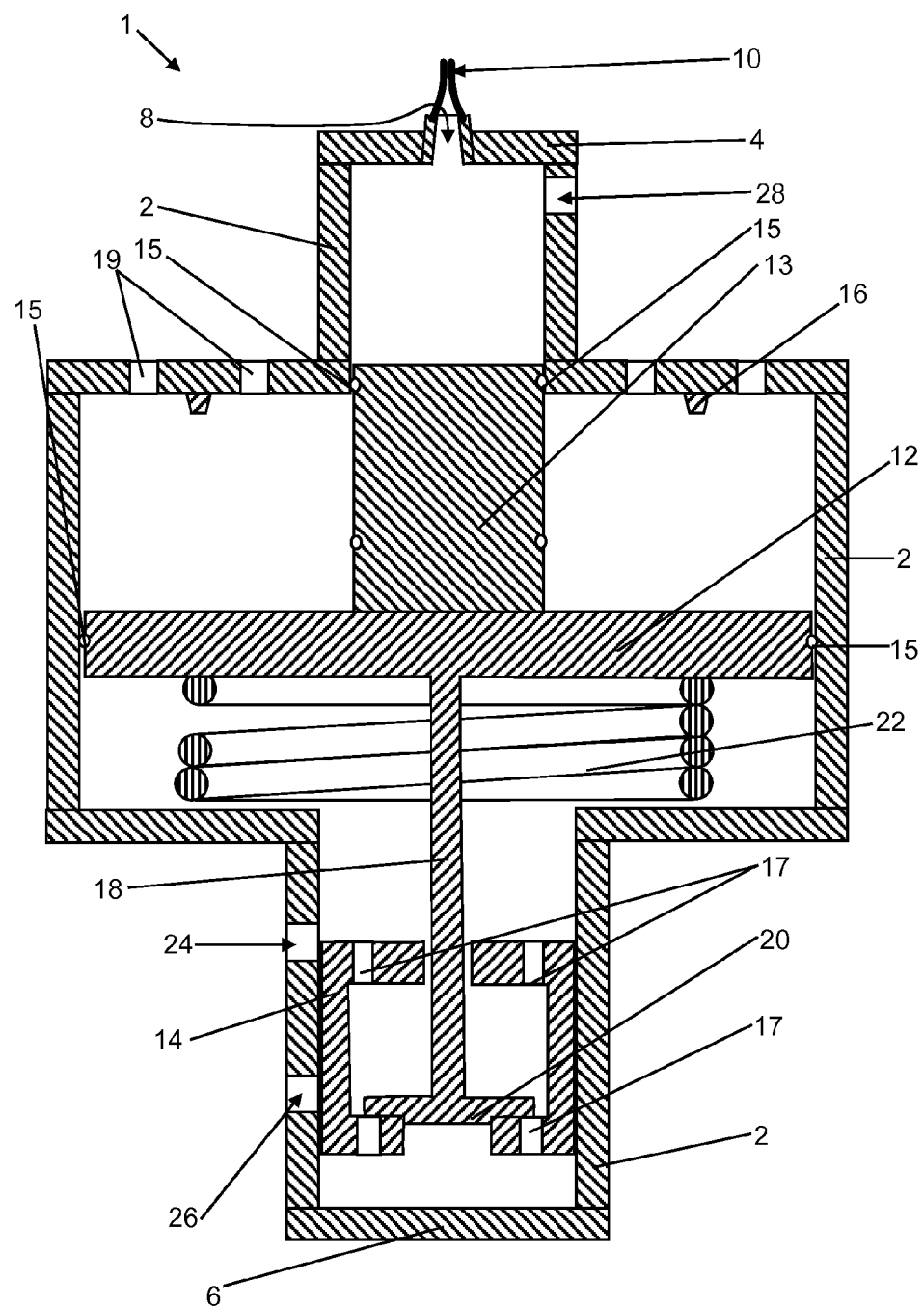
Figure 6:
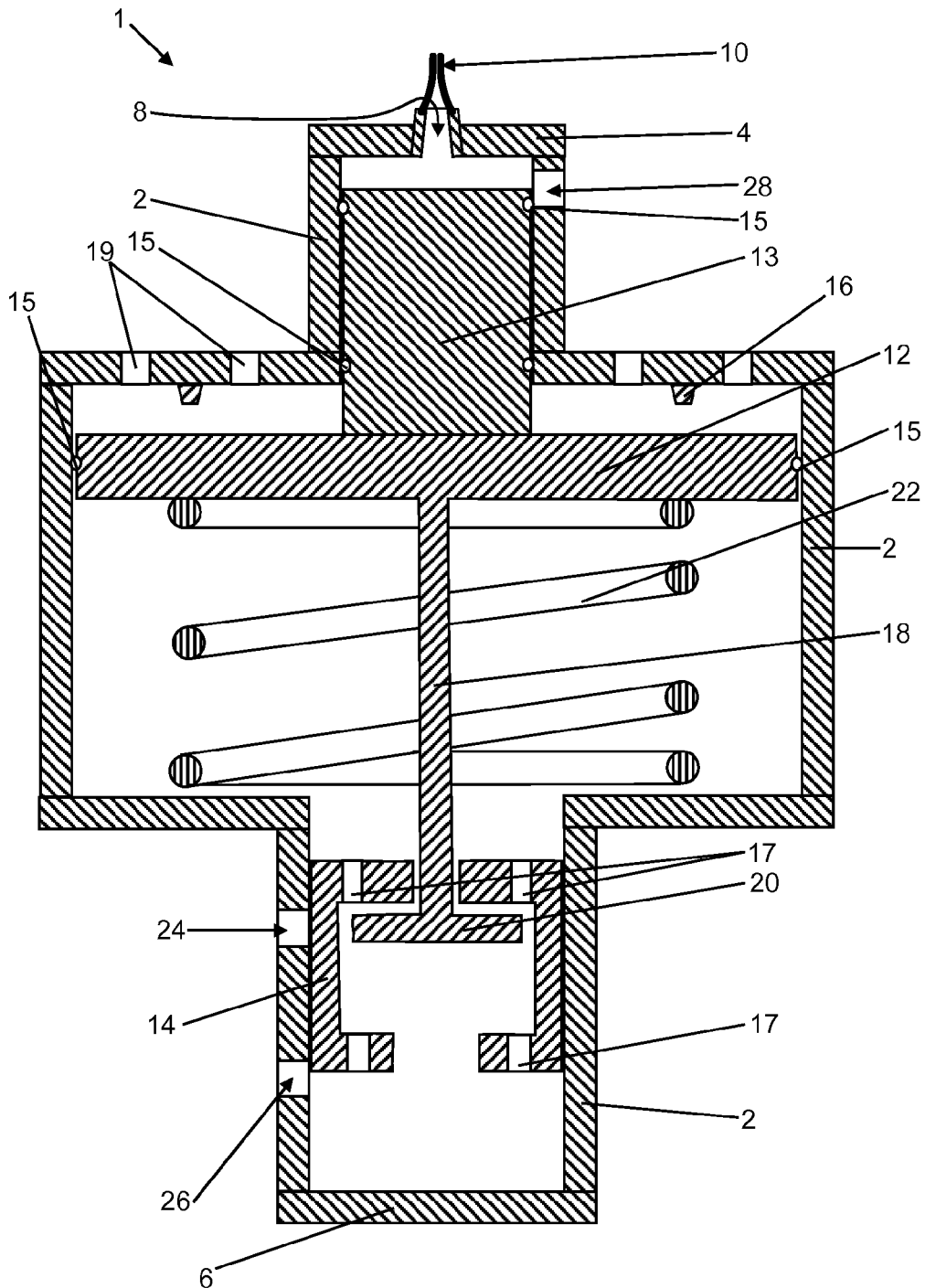
Figure 7:
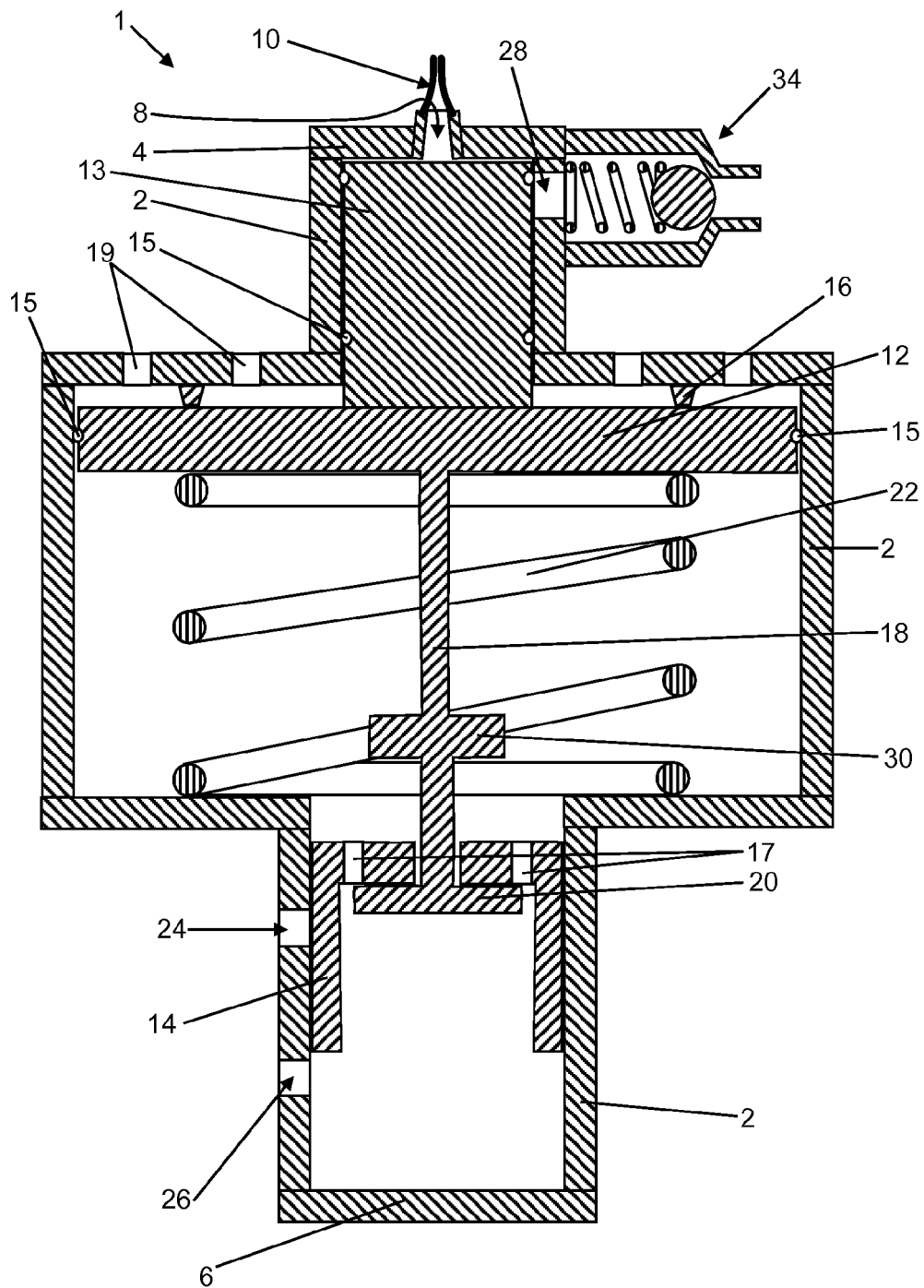
Figure 8:
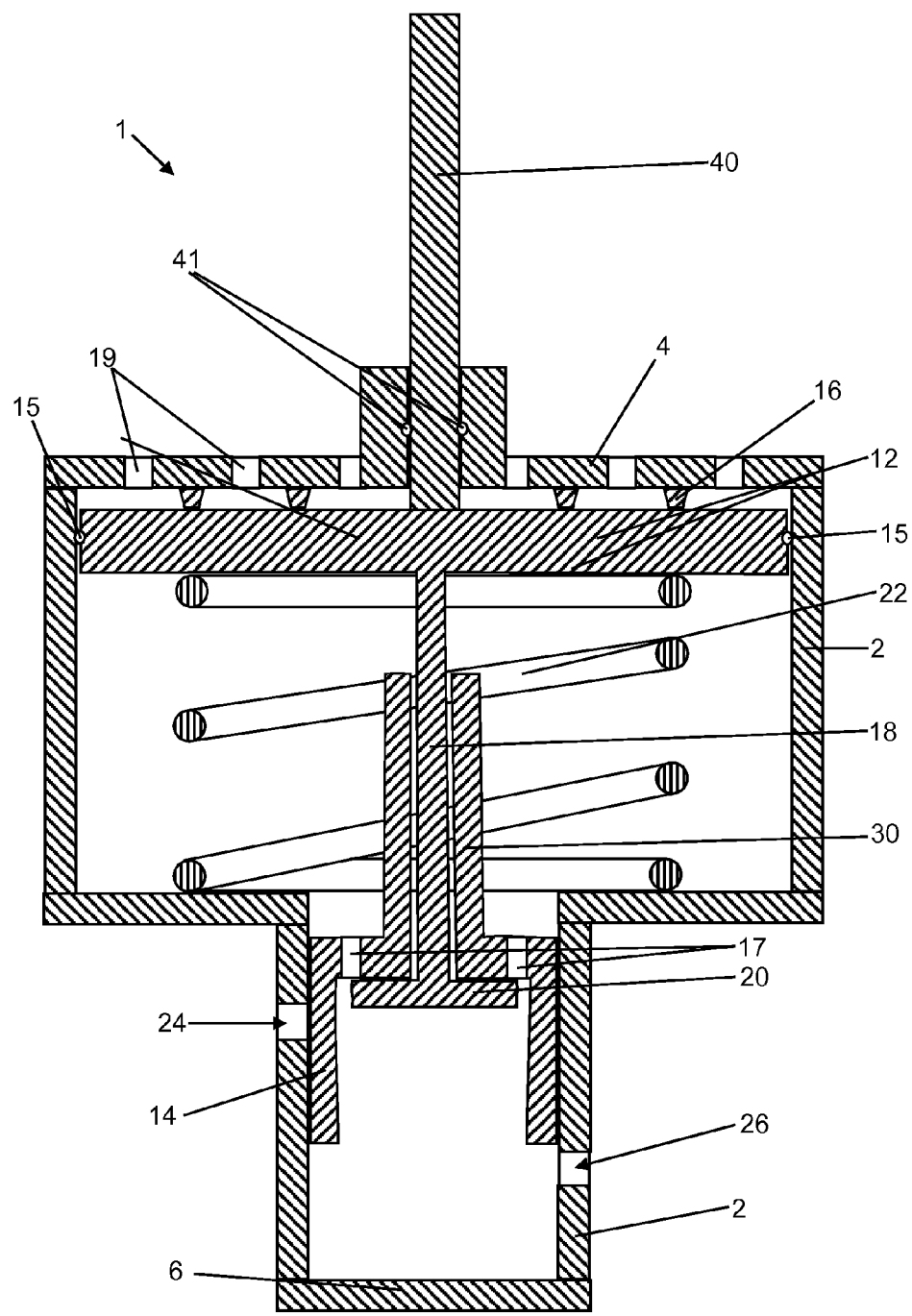
Figure 9:
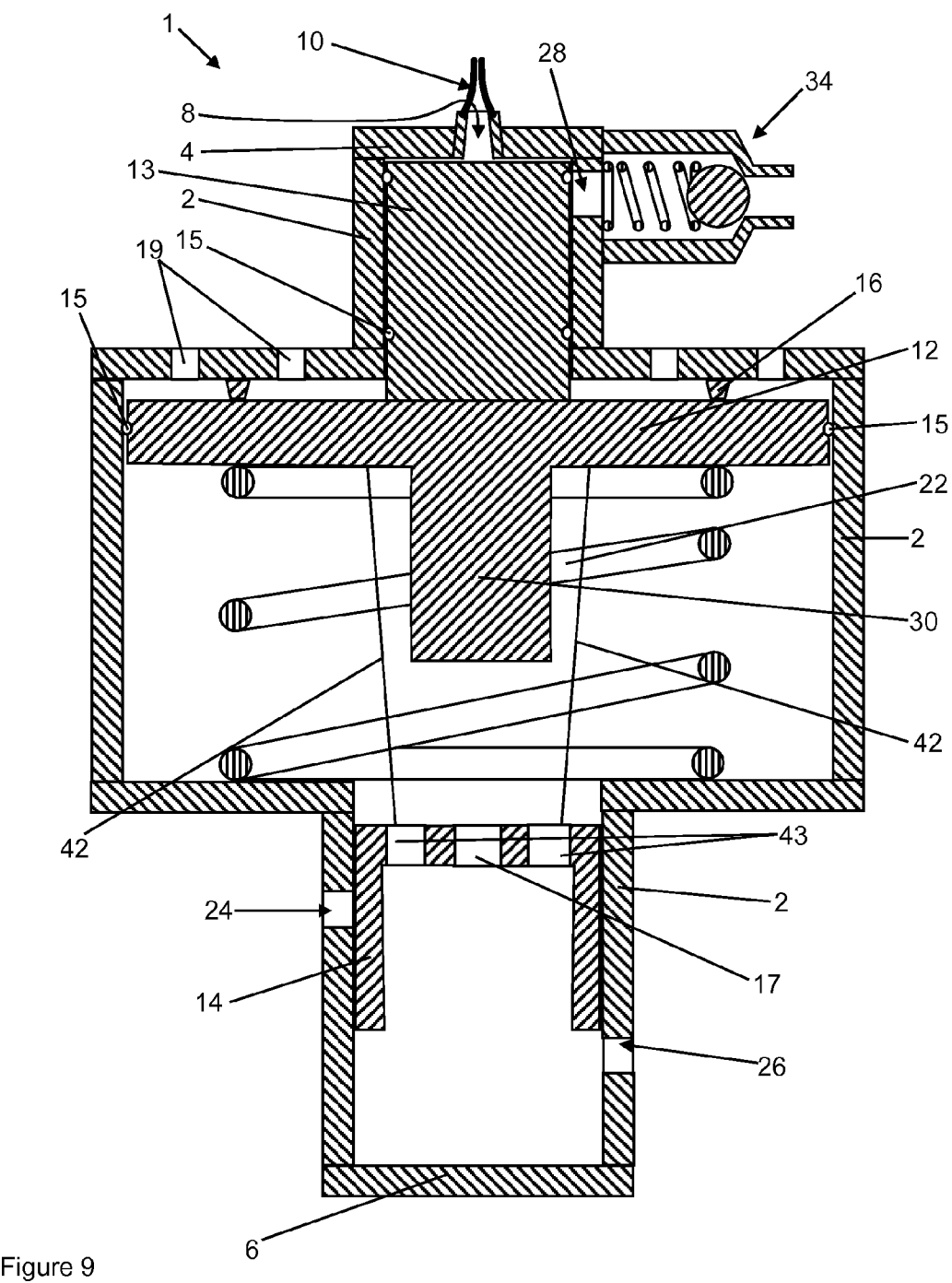
Figure 10:
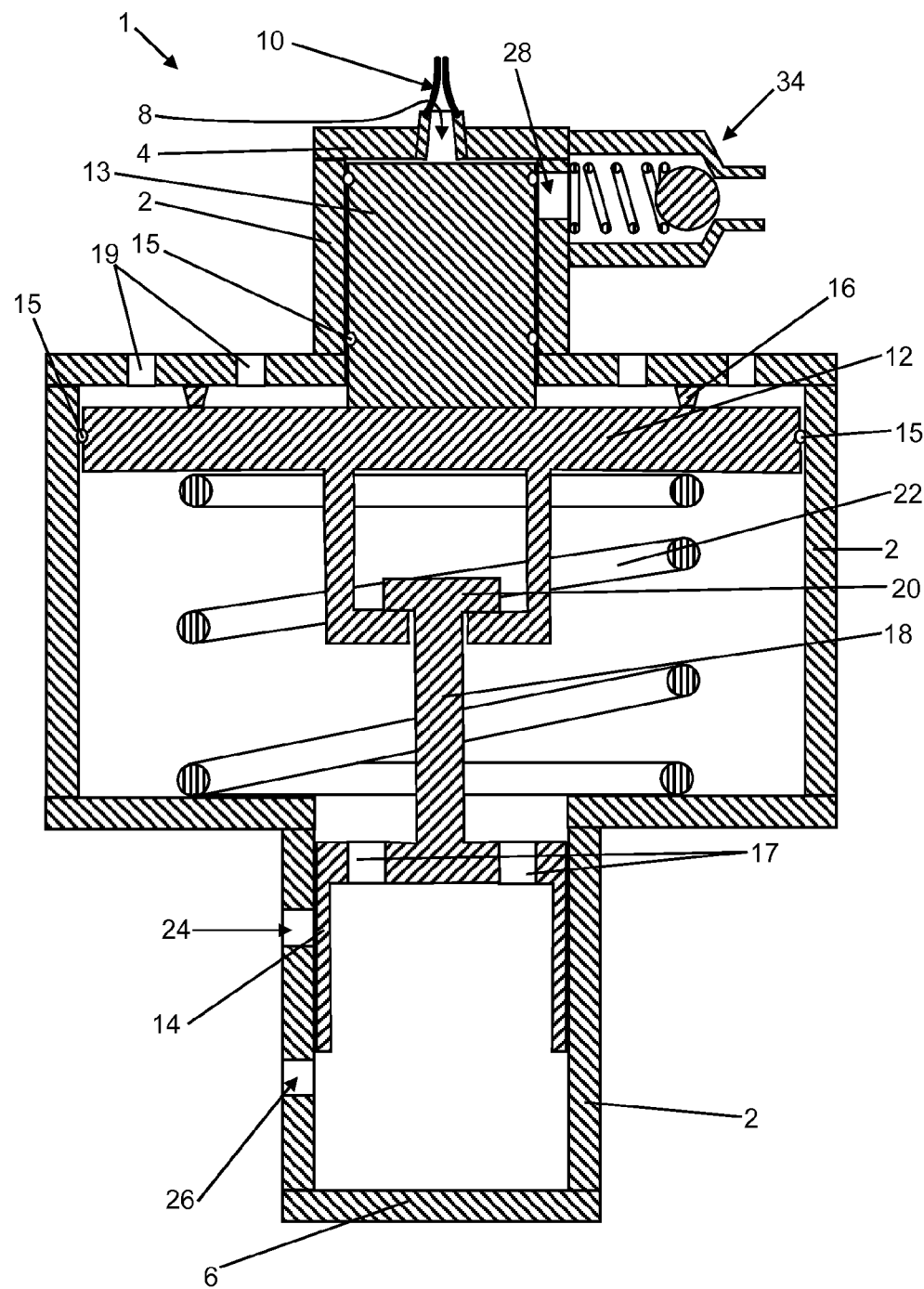
Figure 11:
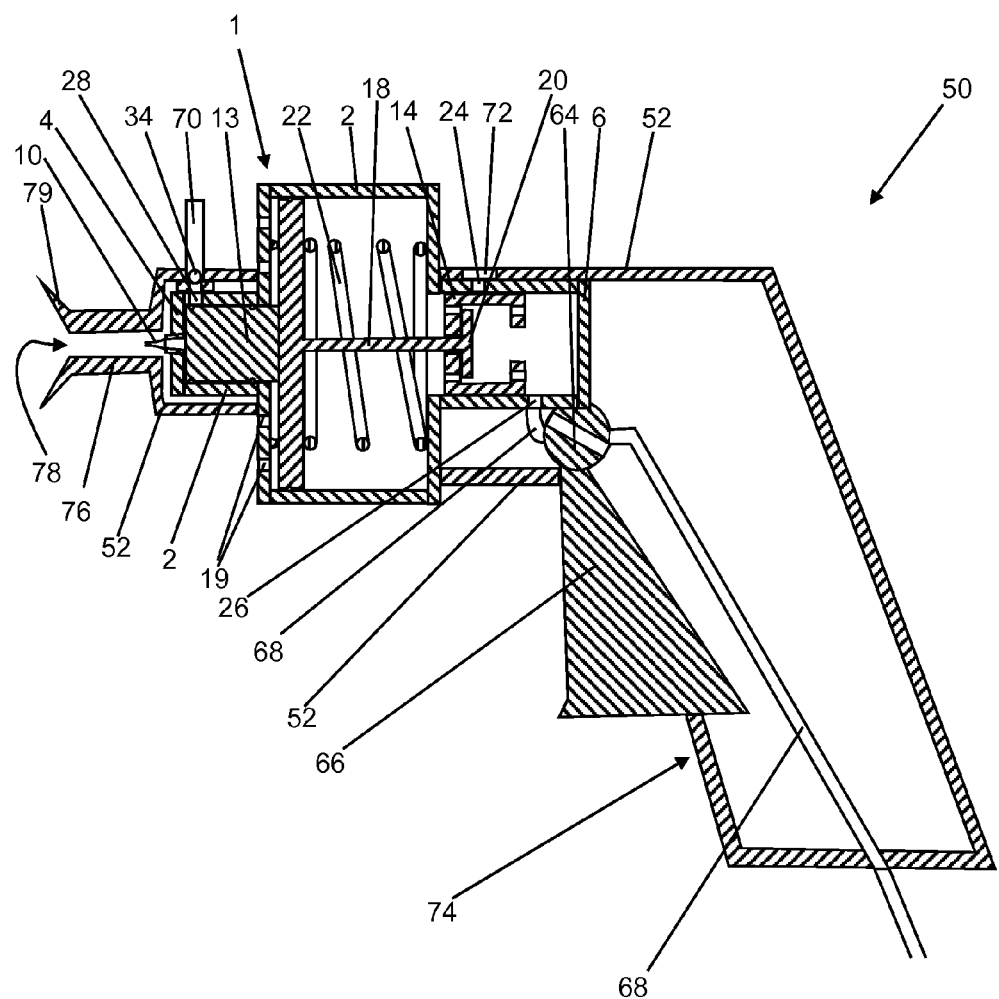

Further exemplary embodiments of the invention shall be illustrated in the following on the basis of eleven schematic figures, though without limiting the scope of the invention. In the figures:

FIG. 1: shows a schematic cross-sectional view of a vacuum motor according to the invention in the starting state and/or the start position, in which the gas inlet opening is closed and the gas outlet opening is open;

FIG. 2: shows a schematic cross-sectional view of the inventive vacuum motor according to FIG. 1, in which the working plunger is moved by the vacuum or pressure difference;

FIG. 3: shows a schematic cross-sectional view of the inventive vacuum motor according to FIG. 1, in which the catch of the working plunger hits against the control plunger;

FIG. 4: shows a schematic cross-sectional view of the inventive vacuum motor according to FIG. 1, in which the working plunger shifts the control plunger appropriately such that the gas inlet opening and the gas outlet opening are closed;

FIG. 5: shows a schematic cross-sectional view of the inventive vacuum motor according to FIG. 1, in which the working plunger shifts the control plunger appropriately such that the gas inlet opening is open and the gas outlet opening is closed;

FIG. 6: shows a schematic cross-sectional view of the inventive vacuum motor according to FIG. 1, in which the working plunger is moved again in reverse direction by the resetting element and the control plunger has again been pulled in the direction of the front side;

FIG. 7: shows a schematic cross-sectional view of an alternative vacuum motor according to the invention having a spacer on the catch pin and a non-return valve on the liquid supply opening;

FIG. 8: shows a schematic cross-sectional view of another alternative vacuum motor according to the invention having a spacer on the control plunger and a rod for forming a thrusting motor;

FIG. 9: shows a schematic cross-sectional view of a fourth alternative vacuum motor according to the invention having a string or a cable as catch element, and a non-return valve;

FIG. 10: shows a schematic cross-sectional view of a fifth alternative vacuum motor according to the invention, in which the catch element is fastened to the control plunger; and FIG. 11: shows a schematic cross-sectional view of a lavage system according to the invention having a vacuum motor according to the invention.

Identical or similar components are identified in the figures, to some extent, through the same reference numbers even if different vacuum motor are concerned.

FIGS. 1 to 6 show schematic cross-sectional views of a vacuum motor 1 according to the invention in chronological order during a working cycle. The cross-sections contain the symmetry axis of the components of the vacuum motor 1, i.e. the cross-section cutting through the middle is depicted. The vacuum motor 1 comprises a hollow body 2 that is made of plastic material and has a three-part cylindrical internal space. The internal space is closed through a cover plate 4 on the front side and through a rear plate 6 on the rear side. An ejection opening 8 for dispensing a jet of liquid is provided in the cover plate 4. Accordingly, the vacuum motor 1 is well-suited and designed for generating a pulsed jet of a rinsing liquid from the ejection opening 8.

The ejection opening 8 is closed by means of a lip valve 10, which opens when a liquid is ejected from the front internal space, i.e. when the pressure in the front internal space is high enough. This means that the pressure in the front internal space is higher than the ambient pressure plus the elastic force of the lip valve 10. The rear plate 6 closes the rear-side, i.e. rear, internal space of the hollow body 2 in gas-tight and pressure-tight manner. A working plunger 12 is situated in the middle internal space, which can be called working space, and is arranged to be mobile along the cylinder axis of the cylindrical internal space and/or of the middle internal space. A cylindrical pump plunger 13 is situated in the front internal space, which can be called pump space, and is arranged to be mobile along the cylinder axis of the cylindrical internal space and/or of the front internal space. A control plunger 14 is situated in the rear internal space, which can be called valve space, but also can have the work-performing gas of the vacuum motor 1 passed through it, and is arranged to be mobile along the cylinder axis of the cylindrical internal space and/or of the rear internal space. The working plunger 12 touches by its entire circumference against the cylinder walls of the middle internal space and, for this purpose, is sealed with respect to the internal walls of the middle internal space by means of a sealing ring 15 made of rubber or any other elastic material. The pump plunger 13 touches by its entire circumference against the cylinder walls of the front internal space and, for this purpose, is sealed with respect to the internal walls of the front internal space by means of a sealing ring 15 made of rubber or any other elastic material. The control plunger 14 touches tightly and by its entire circumference against the cylinder walls of the rear internal space. Likewise, the control plunger 14 can be sealed with respect to the internal wall of the rear internal space by means of sealing rings (not shown). The sealing rings 15 touch by the entire circumference against the working plunger 12 and the pump plunger and the internal walls of the hollow body 2. The working plunger 12 and the pump plunger 13 are preferably made to be the same single part and are made of plastic material.

The diameter of the middle internal space perpendicular to the cylinder axis is approximately thrice the diameters of the front internal space and of the rear internal space, and thus the cross-sectional surface area is approximately ninefold larger than the cross-sectional surface area of the front internal space and of the rear internal space. As a result, the middle internal space comprises a front wall in the front and a rear wall in the rear (on the rear side) that connect the walls 2 of the middle internal space to the walls 2 of the front and rear internal spaces. The working plunger 12 is situated at a distance from the front wall of the middle internal space by means of multiple spacers 16, which ensure that the working plunger 12 cannot touch against the front wall of the middle internal space and get sucked against it. Moreover, ventilation openings 19 are provided in the front wall of the middle internal space that facilitate a gas exchange between the surroundings and the region between the front wall of the middle internal space and the working plunger 12. As a result, a negative pressure in this region does not impede the motion of the working plunger 12 away from the front wall of the middle internal space and/or an overpressure in this region does not impede the motion of the working plunger 12 towards the front wall of the middle internal space. The invention can therefore provide the front wall of the middle internal space to be implemented by means of a grid. This renders the gas exchange feasible with particularly little flow resistance.

The control plunger 14 is also made of plastic material and takes the basic shape of a tube having a front cover and a rear cover which are oriented such as to be perpendicular to the cylinder axis. It is self-evident that the covers can just as well take different shapes and be inclined differently. Passages 17 are arranged in the covers and are to enable a gas exchange between the two sides of the control plunger 14. Another central passage on the symmetry axis is provided within the spacer 16.

The control plunger 14 is arranged between the working plunger 12 and the rear plate 6 such as to be mobile in the rear internal space. A catch unit consisting of a catch pin 18 and a catch 20 is fastened to the working plunger 12. The catch pin 18 and the working plunger 12 are preferably provided as the same single part and are also made of plastic material. The catch pin 18 is a cylindrical rod that extends through the axial passage in the front cover of the control plunger 14. The catch 20 is a flat disc that does not fit through the central passages in the covers of the control plunger 14. The shape of the catch 20 is not essential and can, but does not have to, be adapted to match the shape of the covers of the control plunger 14.

A steel spring 22 is arranged between the rear wall of the middle internal space and the working plunger 12 as resetting element 22 in the middle internal space. The control plunger 14 covers a lateral gas inlet opening 24 that is connected to a compressed gas or, preferred according to the invention, that is open towards the surroundings of the vacuum motor 1. In the latter case, ambient air at atmospheric pressure of the surroundings can then be supplied into the vacuum motor 1 when the gas inlet opening 24 is open. The gas inlet opening 24 and a gas outlet opening 26 are situated in the side wall (the cylinder jacket) of the hollow space 2 in the rear internal space. The steel spring 22 pushes the working plunger 12 onto the spacers 16 on the front wall of the middle internal space such that the control plunger 14 is held in the position shown when no vacuum or negative pressure (a gas at a pressure below ambient pressure) is applied through a gas outlet opening 26 into the rear [internal space] and from there also into the middle internal space. It is also sufficient that the steel spring 22 effects a sufficient resetting force to act on the working plunger 12 during the working process of the vacuum motor 1. Preferably, the steel spring 22 is sufficiently long such that it pushes the working plunger 12 onto the spacers 16 in the starting state shown in FIG. 1. This ensures that the gas outlet opening 26 remains open when no negative pressure is applied to the vacuum motor 1 and it ensures that the vacuum motor 1 is always transitioned into the starting state according to FIG. 1.

The gas inlet opening 24 is a through-going opening in the side wall of the hollow body 2. Aside from the gas inlet opening 24, the gas outlet opening 26 and a liquid supply opening 28 are provided in the side wall of the hollow body 2. The liquid supply opening 28 is situated in the side wall and/or the cylinder jacket wall of the front internal space, i.e. in the pump space. In the starting state of the vacuum motor 1 shown in FIG. 1, the gas outlet opening 26 is not closed and/or is not covered by the control plunger 14. The working medium (the gas and/or air) is drawn out of the internal space through the gas outlet opening 26, when the gas outlet opening 26 is exposed by the control plunger 14 being in a suitable position (as shown in FIG. 1). In contrast, the liquid supply opening 28 is arranged between the working plunger 12, and/or the pump plunger 13, and the cover plate 4 and is intended for filling the front internal space with a liquid, which is then extruded through the ejection opening 8 upon a motion of the working plunger 12, and/or of the pump plunger 13, towards the cover plate 4 (as shown in FIG. 6) and thus generates a spray jet and/or a spray cone (not shown).

FIG. 1 shows the starting state of the vacuum motor 1. A negative pressure is applied to the internal space between the working plunger 12 and the rear plate 6 via the gas outlet opening 26. The decreasing pressure in this intervening space accelerates the working plunger 12 in the direction of the rear plate 6, i.e. towards the rear side of the vacuum motor 1. To be exact, the pressure difference between the front side of the working plunger 12 in the middle internal space and the rear side of the working plunger 12 in the middle internal space accelerates the working plunger 12 in the direction of the rear plate 6. The control plunger 14 stays in place in this context. The compression spring 22 is being compressed and tensioned upon the motion of the working plunger 12. The compression spring 22 takes up energy during this process. This situation is shown in FIG. 2.

The motion of the pump plunger 13 causes a liquid to be drawn through the liquid supply opening 28 into the front internal space. For this purpose, the front internal space is closed, except for the liquid supply opening 28, by means of the pump plunger 13 having the seals 15 and the hollow space 2 having the cover plate 4. The lip valve 10 closes due to the negative pressure in the front internal space. The supply of liquid continues for as long as the working plunger 12 and thus the pump plunger 13 move in the direction of the rear plate 6.

During the motion of the working plunger 12, the working plunger 12 compresses the spring element 22. When the working plunger 12 has moved towards the control plunger 14 to the extent that the length to the rear limit stop on the rear-side cover is bridged by the catch pin 18 and the catch 20, the catch 20 hits against the rear-side cover of the control plunger 14 (this situation is shown in FIG. 3) and hits it backwards. The control plunger 14 is then pushed along by the working plunger 12 by means of the catch element 18, 20. As a result, the control plunger 14 moves towards the rear plate 6. The gas outlet opening 26 becomes covered and/or closed through the motion of the control plunger 14. This situation is shown in FIG. 4.

During the whole time, the front internal space between the pump plunger 13 and the cover plate 4 is being filled with rinsing liquid through the liquid supply opening 28. Due to the inertia of the working plunger 12 and/or control plunger 14 and/or the negative pressure that is still present in the internal space between the working plunger 12 and the rear plate 6, the control plunger 14 is moved backward even further and the gas inlet opening 24 is being opened. This situation is shown in FIG. 5.

Subsequently, the gas flows from the surroundings or from a compressed gas reservoir through the gas inlet opening 24 into the internal space between the working plunger 12 and the rear plate 6. The spring element 22 accelerates the working plunger 12 in the direction of the cover plate 4. Since the volume between the pump plunger 13 and the cover plate 4 decreases, an over-pressure is generated and the lip valve 10 opens. Preferably, a non-return valve (not shown) is arranged on the liquid supply opening 28 and prevents the liquid from exiting from the intervening space between the working plunger 12 and the cover plate 4 into the liquid supply. The liquid or the liquid-gas mixture in the front internal space is pushed out and/or extruded out of the front internal space through the ejection opening 8 by means of the pump plunger 13. This generates a spray jet of the rinsing liquid.

The motion of the working plunger 12 detaches the catch 20 from the limit stop of the rear cover of the control plunger 14. The working plunger 12 finally hits against the front cover of the control plunger 14. This also moves the control plunger 14 in the direction of the cover plate 4 again and the gas inlet opening 24 closes again and the gas outlet opening 26 begins to open. This condition is shown in FIG. 6.

After the gas outlet opening 26 is opened fully, the spring element 22 has transitioned the working plunger 12 and the control plunger 14 back into the starting state shown in FIG. 1. Concurrently, the rinsing liquid or the liquid-gas mixture has been ejected fully from the intervening space between the working plunger 12 and the cover plate 4 through the ejection opening 8. The cycle starts up again from the beginning.

The control plunger 14 and its motion effect an automatic valve control of the gas inlet opening 24 and gas outlet opening 26 such that the control plunger 14 can be considered to be a valve element.

Due to the action of the resetting element 22, the liquid present in the hollow space is extruded through the ejection opening 8 and the outlet valve 10 during the motion of the working plunger 12 in the direction of the cover plate 4. A non-return valve (not shown) arranged on the liquid supply opening 28 prevents the liquid from exiting into the liquid reservoir. After the gas outlet opening 26 is opened and the working plunger 12 moved in the direction of the rear plate 6, the action of the vacuum and/or negative pressure, in concert with the compressed gas or ambient pressure, generates a negative pressure in the front internal space. In this context, the non-return valve opens and the liquid flows into the front internal space.

Once the gas outlet opening 26 closes, the resetting element 22 pushes the working plunger 12 back into its starting position, whereby the over-pressure closes the non-return valve and liquid is pushed out of the front internal space. Then, the liquid pumping process proceeds in the manner described for as long as vacuum or a negative pressure is being applied to the gas outlet opening 26 and for as long as liquid is present in the liquid reservoir.

FIG. 7 shows a schematic cross-sectional view of an alternative vacuum motor 1 according to the invention having a spacer 30 on the catch pin 18. The spacer 30 can extend as a fin in both directions radially away from the catch pin 18 or can be formed by a circular disc that extends radially perpendicular from the catch pin 18 into the interior of the middle internal space or of the rear internal space (depending on the position of the working plunger 12 in the hollow body 2). The control plunger 14 needs just a front cover in this embodiment. Compared to the embodiment according to FIGS. 1 to 6, this embodiment according to FIG. 7 has no rear cover on the control plunger 14. But the control plunger 14 of said vacuum motor 1 has two limit stops for the catch 20 and the spacer 30 on the catch pin 18, which are formed by the front side and the rear side of the single (front) cover in this embodiment. In the embodiment according to FIGS. 1 to 6, these two limit stops are instead formed by the rear side of the front cover and by the front side of the rear cover.

The feed-through through the control plunger 14 of the vacuum motor 1 according to FIG. 7 through which the catch pin 18 extends also serves for gas exchange between the intervening space between the working plunger 12 and the control plunger 14 and the intervening space between the control plunger 14 and the rear plate 6. Theoretically, there is no need to have additional passages 17. In order to perform work on the working plunger 12, i.e. in order to allow the vacuum to act on the rear side of the working plunger 12, it is important though to have a sufficiently gas-permeable connection present that has a sufficient cross-section and/or a low gas flow resistance. Not only the passages 17 and the feed-through for the catch pin 18, but also the intervening spaces between the control plunger 14 and the internal cylinder wall of the rear internal space can be used for this purpose. Recesses that extend in the internal walls 2 of the rear internal space along the entire length of the external walls of the control plunger 14 and/or extend along the entire length of the swept volume of the control plunger 14 can be provided for this purpose.

Moreover, the vacuum motor 1 is drawn in FIG. 7 to also have a non-return valve 34 on the liquid supply opening 28. In all other respects, the structure and functional principle are identical to those shown in FIGS. 1 to 6 and described above.

The tension spring 22 pushes the working plunger 12 so far in the direction of the cover plate 4 that the front side of the catch 20 touches against the rear side of the cover of the control plunger 14 and thus the control plunger 14 is pulled appropriately in the direction of the front side (the cover plate 4) such that the gas outlet opening 26 is exposed and the gas inlet opening 24 is closed. Preferably, the compression spring 22 then still exerts a force on the working plunger 12 that pushes the working plunger 12 in the direction of the cover plate 4. When a vacuum or a negative pressure acts through the gas outlet opening 26, the working plunger 12 is pulled in the direction of the control plunger 14 and/or in the direction of the rear plate 6, and the compression spring 22 is concurrently being tensioned. The control plunger 14 is accelerated in the direction of the rear plate 6 when the spacer 30 hits against the front side of the cover of the control plunger 14. Therefore, the difference as compared to the embodiment according to FIGS. 1 to 6 is that the rear side of the spacer 30, rather than the rear side of the catch 20, accelerates the control plunger 14. In all other respects, the operating principle of the vacuum motor 1 according to FIG. 7 corresponds to the functional principle of the vacuum motor 1 according to FIGS. 1 to 6.

The non-return valve 34, which, in the same design, can also be arranged on the liquid supply openings 28 of other vacuum motors according to the invention, like the one according to FIGS. 1 to 6, consists of a ball that is pressed onto a ball seat by means of a steel spring. This enables a flow through the liquid supply opening 28 into the front internal space of the hollow body 2, whereas a flow out of the internal space is blocked through the non-return valve 34. Accordingly, if the content of the vacuum motor 1 between the pump plunger 13 and the cover plate 4 is sprayed out through the ejection opening 8 by means of a motion of the working plunger 12 towards the cover plate 4, the non-return valve 34 prevents the content from advancing into the supply line.

The compressed gas-driven liquid pump 1 works such that a hollow space (as part of the front internal space) is present on the front side of the pump plunger 13. Said hollow space is connected in liquid-permeable manner to the non-return valve 34 that enables an inflow of liquid from a liquid reservoir into the hollow space and prevents the liquid from flowing in reverse from the hollow space in the direction of the liquid reservoir. Moreover, an outlet valve 10 is connected to the hollow space in liquid-permeable manner. Said outlet valve enables the liquid to flow out of the hollow space and prevents the liquid from flowing back into the hollow space. Said outlet valve 10 can be a lip valve 10 in the simplest case. The basic functional principle of the vacuum motor 1 is as described above.

FIG. 8 shows a schematic cross-sectional view of a third alternative vacuum motor 1 having a spacer 30, which is arranged on a control plunger 14 and/or is provided as the same part as the control plunger 14, and having a rod 40 for forming a thrusting vacuum motor 1. The structure of the vacuum motor 1 is the same as that of the vacuum motors according to FIGS. 1 to 6 and 7 described above, whereby the following differences are present in addition to the differences mentioned previously. The vacuum motor 1 comprises a hollow body 2 that has only a two-part cylindrical internal space. The front internal space is covered by a cover plate 4 on the front side and the rear internal space is closed on the rear side by a rear plate 6 in gas- and pressure-tight manner. Accordingly, compared to the embodiments according to FIGS. 1 to 7, the front-most internal space is missing (the middle internal space according to FIGS. 1 to 7 corresponds to the front internal space according to FIG. 8).

A working plunger 12 is arranged in the front internal space such as to be mobile in linear direction along the cylinder axis of the internal space. The control plunger 14 is arranged between the working plunger 12 and the rear plate 6 such as to be mobile in linear direction along the cylinder axis of the rear internal space. Working plunger 12 and control plunger 14 comprise a cylindrical outer jacket that corresponds to the inner cylinder jacket of the internal space.

The working plunger 12 is sealed with respect to the internal wall of the front internal space through a sealing ring 15. The cross-section of the front internal space is approximately nine-fold larger than the cross-section of the rear internal space. Accordingly, the working plunger 12 has an approx. three-fold larger diameter than the control plunger 14. Multiple short spacers 16 in the form of truncated cones are arranged on the rear side of the cover plate 4 and are to prevent the working plunger 12 from becoming placed against the cover plate 4. Moreover, the cover plate 4 comprises ventilation openings 19 through which air from the surroundings of the vacuum motor 1 can be drawn in. As a result, no or only very small pressure fluctuations that would act against a motion of the working plunger 12 arise in the intervening space between the front side of the working plunger 12 and the cover plate 4. Passages 17 are arranged in the control plunger 14 and enable a gas exchange between the front side and the rear side of the control plunger 14.

A catch element consisting of a catch pin 18 and a catch 20 is arranged on the rear side of the working plunger 12. The catch pin 18 extends through a feed-through in the control plunger 14 such that the catch 20 can engage on the rear side of a surface perpendicular to the cylinder axis of the control plunger 14 in order to pull the control plunger 14 along at a distance to the working plunger 12 when the working plunger 12 moves in the direction of the front side, i.e. in the direction of the cover plate 4. Said surface and/or said limit stop corresponds to the rear side of the front cover according to FIGS. 1 to 6 and to the single cover according to FIG. 7.

Rather than provide a spacer on the catch pin 18 (as proposed in the embodiment according to FIG. 7), the embodiment according to FIG. 8 provides, on the control plunger 14, a spacer 30 in the form of a cylindrical tube whose front surface serves as second limit stop onto which the working plunger 12 hits when it moves in the direction of the rear plate 6. The spacer 30 can just as well be formed by rods or any other geometrical shape that does not impede the gas exchange between the front side and the rear side of the control plunger 14 and the motion of the spring element 22 and of the working plunger 12.

The front internal space between the working plunger 12 and the rear plate 6 and/or the rear wall of the front internal space has a spring element 22 arranged in it and about the catch pin 18 as compression spring 22 that pushes the working plunger 12 in the direction of the cover plate 4. FIG. 8 therefore shows the starting position of the vacuum motor 1.

Two through-going openings 24, 26 are provided in the side wall of the hollow body 2. The gas inlet opening 24 is open towards the outside such that ambient air can be supplied into the vacuum motor 1. During the working cycle of the vacuum motor 1, the air is drawn and/or evacuated partially or largely from the internal space of the hollow body 2 behind the working plunger 12 through the gas outlet opening 26. The working cycle proceeds as described through the first exemplary embodiment according to FIGS. 1 to 6.

Instead of ejecting a liquid periodically, as with the lavage pumps according to FIGS. 1 to 7, the vacuum motor 1 according to FIG. 8 attains periodical thrusting of the rod 40. The rod 40 is guided out of the internal space, by means of a guide sleeve 41, through an opening in the cover plate 4. Alternatively, instead of the rod 40 being rigidly connected to the working plunger 12, a plunger rod 40 can be connected to the working plunger 12 by means of a joint (not shown) that is guided through the cover plate 4. The plunger rod 40 can be used to translate the periodical linear motion into a rotary motion by means of a crankshaft (not shown) that is fastened in the front to the plunger rod 40 by means of a joint. Accordingly, the vacuum motor 1 according to FIG. 8 comprises no pump plunger.

The vacuum motor 1 according to FIG. 8 can also be used in a lavage system. For this purpose, the tip of the rod 40 is used to hit against a membrane (not shown). The periodical impact on the membrane can be used for periodical ejection of a liquid. Likewise, the periodical motion of the rod 40 can be used as a drive for a shaking mechanism or a rapping motor.

Alternatively, the vacuum motor 1, if provided with a plunger rod 40, can be used to drive a cutting disc or a pump.

FIG. 9 shows a schematic cross-sectional view of a fourth alternative inventive vacuum motor 1 having a string 42 or a cable 42 as catch element 42, and having a non-return valve 34. The structure and arrangement of the non-return valve 34 correspond to the description of the structure and arrangement according to FIG. 7. In this version of the vacuum motor 1, the spacer 30 is arranged as a solid cylinder on the rear side of the working plunger 12. As before, the working plunger 12 is sealed with respect to the internal walls of the middle cylindrical internal space in the hollow body 2 by means of an O-ring 15.

In the position of the vacuum motor 1 shown in FIG. 9, the cables 42 are tensioned. The working plunger 12 pulls the control plunger 14 along in trailing manner in the direction of the cover plate 4 by the cables 42 in order to close the gas inlet opening 24 and to then open the gas outlet opening 26. The cables 42 are fastened to struts 43 on the front side of the control plunger 14, for example are tied around the struts 43 by means of a loop.

When the working plunger 12 is pulled in the direction of the rear plate 6, the cables 42 are loosely attached in the middle internal space between the working plunger 12 and the control plunger 14. Only when the control plunger 14 is pulled along by the working plunger 12, the cables 42 or strings 42 are tensioned to be taut, as shown in FIG. 9.

The front side of the control plunger 14 then forms the sole limit stop against which the working plunger 12 and/or spacer 30 of the working plunger 12 hits in order to push the control plunger 14 in the direction of the rear plate 6 and to thereby close the gas outlet opening 26 and to then open the gas inlet opening 24. Accordingly, the embodiment according to FIG. 9 has just a single limit stop. The gas inlet opening 24 and gas outlet opening 26 do not have to be situated adjacent to each other, but rather can, as shown in FIG. 9, be arranged in the cylinder jacket opposite from each other or at different places of matching height of the cylinder axis of the rear internal space.

FIG. 10 shows a schematic cross-sectional view of a fifth alternative inventive vacuum motor 1, in which the catch element 18, 20 is fastened to the control plunger 14. In this embodiment, the catch element 18, 20 runs into a hollow space in the working plunger 12. A structure is arranged on the rear side of the working plunger 12 for this purpose. Since the catch pin 18 is longer than the hollow space in the working plunger 12 is deep, it also assumes the task of a spacer that ensures that the working plunger 12 is definitely situated at a distance from the control plunger 14 when the working plunger 12 pushes the control plunger 14 in the direction of the rear plate 6.

The passages 17 in the control plunger 14 are necessary to allow the gas in the vacuum motor 1 to flow from the rear side of the working plunger 12 through the control plunger 14 to the gas outlet opening 26 and to finally flow out through the gas outlet opening 26 when said opening is opened by the control plunger 14.

Accordingly, the two limit stops of the embodiment according to FIG. 10 are formed, with respect to the control plunger 14, by the front side and rear side of the catch 20 and are formed, with respect to the working plunger 12, by the front-side internal surface in the hollow space and/or in the structure on the rear side of the working plunger 12 and by the rear-side surface of the hollow space of the structure on the rear side of the working plunger 12.

FIG. 11 shows a schematic cross-sectional view of a lavage system 50 according to the invention that can be held in one hand and has a vacuum motor 1 according to the invention. Except for the arrangement of the gas inlet opening 24 and gas outlet opening 26 with respect to each other, the vacuum motor 1 is structured alike the vacuum motor 1 according to FIGS. 1 to 6 such that reference shall be made to said exemplary embodiment with respect to the structure. With the exception of the vacuum motor according to FIG. 8, the other exemplary embodiments can also used, by slight adaptation, as vacuum motor 1 or pump motor 1 in the present lavage system 50.

The lavage system 50 comprises a housing 52 made of plastic material, in which the vacuum motor 1 is arranged. A vacuum or negative pressure is guided via a gas discharge line 68 to a control valve 64. The control valve 64 can be operated manually by means of a trigger 66 of the type of a pistol using the same hand that holds the lavage system 50. The gas feed line 68 continues downstream from the manually operable control valve 64 and is connected to the gas outlet opening 26 of the vacuum motor 1.

The liquid supply opening 28 is connected to a rinsing liquid supply line 70, in which a non-return valve 34 is arranged. An opening 72 is provided on the top of the housing 52 through which ambient air can flow through the gas inlet opening 24 into the vacuum motor 1. The opening 72 can be covered by a grid and/or a filter (not shown) in order to prevent contamination of the interior of the vacuum motor 1.

The gas discharge line 68 and/or the connector 68 to the negative pressure source or vacuum source is guided through in a handle part 74 of the type of a pistol handle, whereby the handle part 74 is formed by the plastic housing 52. Just as well, the liquid line 70 can be guided out on the floor-side of the handle part 74 of the lavage system 50 (not shown). A tube 76 having a dispensing opening 78 and a funnel 79 is arranged on the front side of the lavage system 50 and allows the puffs of rinsing liquid of the vacuum motor 1 to exit or be dispensed from the lavage system 50.

In lavage systems 50 of this type, it is preferred to provide an aspiration facility (not shown) by means of which excess liquid and parts removed along with the liquid are aspirated and discharged via the funnel 79 and the tube 76. Preferably, an aspiration line connected to the aspiration facility is also guided through the floor-side of the handle part 74 for this purpose. When the control valve 64 is operated by means of the trigger 66, the gas discharge line 68 becomes through-going and air is drawn out of the vacuum motor 1 and/or out of the rear internal space and the middle internal space of the vacuum motor 1. The compression spring 22 and/or the resetting element 22 is situated in the middle internal space of the hollow body 2. The pressure difference thus generated between the front side (on the left in FIG. 11) of the working plunger 12 and the rear side (on the right in FIG. 11) of the working plunger 12 puts the working plunger 12 and, delayed by a period of time, the control plunger 14 in motion and the vacuum motor 1 works, as described above. Concurrently, the rinsing liquid conveyed from an external liquid reservoir (not shown) through the liquid supply line 70 flows periodically into the intervening space between the pump plunger 13 and the cover plate 4 of the vacuum motor 1.

The rinsing liquid is ejected from the vacuum motor 1 through periodical puffs through the lip valve 10 and the tube 76 and the dispensing opening 78 for as long as the vacuum or negative pressure is applied to the gas outlet opening 26 and ambient air flows through the gas inlet opening 24 into and through the vacuum motor 1. The process is terminated when the control valve 64 is no longer operated and the gas discharge line 68 is thus interrupted and/or closed. The control valve 64 is restored, for example, by means of an elastic spring (not shown). The working plunger 12 and the control plunger 14 are then positioned in the starting position shown (see FIG. 1 as well) by the spring element 22 in the vacuum motor 1 and the lavage system 50 is immediately ready for use again.

Instead of just one vacuum motor 1, a lavage system 50 can just as well comprise two or more vacuum motors 1, whose vacuum connectors are arranged parallel to each other. This effects a reinforcement of the spray jet thus generated or attains a higher pulse rate, for example a jet of rinsing liquid of doubled frequency.

All embodiments of vacuum motors can just as well be provided to have a second spring element (not shown) in or on the vacuum motor 1 that pushes the control plunger 14 in the direction of the working plunger 12. It is preferred, for this purpose, to have a second compression spring (not shown) arranged between the rear plate 6 and the control plunger 14 in the rear internal space. Said second compression provides added insurance that the starting position is reached when no vacuum and/or negative pressure is applied to the gas outlet opening 26. Moreover, this facilitates travelling over the dead centre (the third position of the control plunger 14), during which both the gas inlet opening 24 and the gas outlet opening 26 are covered and thus closed by the control plunger 14. Moreover, said second spring element can also be utilised to set the working frequency of the vacuum motor 1 and thus to fine-tune the vacuum motor 1.

The features of the invention disclosed in the preceding description and in the claims, figures, and exemplary embodiments, can be essential for the implementation of the various embodiments of the invention both alone and in any combination.

LIST OF REFERENCE NUMBERS

1 Vacuum motor
2 Hollow body/wall
4 Cover plate/front side of the internal space
6 Rear plate/rear side of the internal space
9 Ejection opening
10 Lip valve
13 Pump plunger
12 Working plunger
14 Control plunger
15 Seal/O-ring
16 Spacer/spacing element
17 Passage
18 Catch pin
19 Ventilation opening
20 Catch
22 Spring element/resetting element/compression spring/steel spring
24 Gas inlet opening
26 Gas outlet opening
28 Liquid supply opening
30 Spacer
34 Non-return valve
40 Rod/plunger rod
41 Guide sleeve
42 Cable/string
43 Strut
50 Lavage system
52 Housing
64 Control valve
66 Trigger
68 Gas discharge line/connection to source of negative pressure
70 Rinsing liquid supply line
72 Opening
74 Handle part
76 Tube
78 Dispensing opening
79 Funnel

The invention claimed is:

1. A vacuum motor comprising
  a working plunger,
  an internal space, in which the working plunger is arranged such that it is mobile in linear direction,
  a resetting element that exerts, at least for part of the time, a force on the working plunger that acts in the direction of a front side of the internal space,
  a gas inlet opening for supplying ambient air or a compressed gas into the internal space, and
  a gas outlet opening for discharging the gas from the internal space, wherein the gas outlet opening is connectable to a negative pressure source, whereby a control plunger is arranged between the working plunger and a rear side of the internal space such as to be mobile in linear direction in the internal space, the control plunger, in a first position, does not cover the gas outlet opening and covers the gas inlet opening and, in a second position, does not cover the gas inlet opening and covers the gas outlet opening, the control plunger is supported as in a bearing such as to be mobile with respect to the working plunger, and a catch element and/or a spacer is arranged on said working plunger and/or control plunger, the catch element, upon a motion of the working plunger towards the front side of the internal space, transfers the control plunger into the first position, the catch element or the spacer, upon a motion of the working plunger towards the rear side of the internal space, transfers the control plunger into the second position, and the control plunger, in a third position between the first position and the second position, covers both the gas inlet opening and the gas outlet opening.

2. The vacuum motor according to claim 1, wherein the internal space between the working plunger and the rear side is closed except for the gas inlet opening and the gas outlet opening.

3. The vacuum motor according to claim 1, wherein the catch element, upon a motion of the working plunger away from the control plunger, pulls the control plunger along in the direction of the working plunger and transfers the control plunger into the first position, and the catch element and/or the spacer, upon a motion of the working plunger towards the control plunger, pushes the control plunger in the direction of the rear side and transfers the control plunger into the second position.

4. The vacuum motor according to claim 1, wherein the resetting element is an elastic compression spring that is arranged in the internal space between the working plunger and the rear side of the internal space.

5. The vacuum motor according to claim 1, wherein the control plunger, in the first position, is pulled via the catch element in the direction of the front side by the resetting element, whereby the gas outlet opening opens into the intervening space between the control plunger and the rear side of the internal space.

6. The vacuum motor according to claim 1, wherein at least one gas-permeable passage is arranged in the control plunger and connects the front side of the control plunger facing the working plunger to the rear side of the control plunger facing the rear side of the internal space in gas-impermeable manner.

7. The vacuum motor according to claim 1, wherein the working plunger touches against the internal wall of the internal space by its entire circumference, preferably touches by its entire circumference in gas-tight and pressure-tight manner against the internal space by means of a sealing element.

8. The vacuum motor according to claim 1, an ejection opening is provided in the front side of the internal space opposite from the rear side, and a liquid supply opening is arranged in the front side and/or in the lateral wall of the internal space and the liquid supply opening is not covered by the working plunger at least for part of the time and, in the non-covered state, is arranged between the working plunger and the front side of the internal space.

9. The vacuum motor according to claim 8, wherein the ejection opening is connected to the surroundings by a valve element, in particular a lip valve, whereby the valve element is opened in the presence of sufficient over-pressure as compared to the ambient pressure and is closed otherwise, and in that a tube or a hose with a non-return valve is connected on the liquid supply opening and opens in the presence of a negative pressure in the internal space between the working plunger and the front side of the internal space and thus enables liquid to be supplied into the internal space.

10. The vacuum motor according to claim 8, wherein the working plunger comprises, on the side facing the front side, a pump plunger that has an at least 50% smaller cross-sectional surface area than the part of the working plunger facing the rear side, whereby the cross-section of the internal space is adapted to the cross-section of the pump plunger and to the cross-section of the working plunger.

11. The vacuum motor according to claim 1, wherein the catch element is a string, a cable, a thread, a chain or an elastic spring that is attached to the working plunger and to the control plunger or the catch element comprises a rod, a string, a cable, a thread, a chain or an elastic spring that is attached to the working plunger or to the control plunger and has a catch attached to it that engages, upon the periodical motion of the working plunger, a projection in the working plunger or in the control plunger, whereby the catch element is provided by a rod that is attached to the working plunger and extends through a feed-through in the control plunger and has a catch attached to it that does not fit through the feed-through in the control plunger and engages the feed-through on the rear side of the feed-through of the control plunger in order to pull the control plunger along, when the working plunger is sufficiently far away from the control plunger for this purpose and moves in the direction away from the control plunger.

12. The vacuum motor according to claim 1, wherein the internal space, at least regions thereof, is cylindrical or is cylindrical in the region of a working space of the working plunger or in the entire swept volume of the working plunger and control plunger.

13. The vacuum motor according to claim 1, wherein the working plunger comprises two differently-sized cross-sectional surfaces perpendicular to the linear motion direction of the working plunger, whereby the internal space comprises matching internal walls with different cross-sectional surfaces and the cross-sectional surface on the side of the working plunger facing the rear side is at least 100% larger than the cross-sectional surface of the opposite front side of the working plunger, wherein the cross-sectional surface on the side of the working plunger facing the rear side is at least four times the size of the cross-sectional surface of the opposite front side of the working plunger.

14. The vacuum motor according to claim 1, wherein a second resetting element is arranged in the internal space, which exerts a force on the control plunger in the direction of the working plunger, at least for part of the time, while the vacuum motor is running, whereby an elastic compression spring is arranged between the control plunger and the rear side of the internal space as second resetting element.

15. A lavage system comprising at least one vacuum motor according to claim 1, in which the at least one vacuum motor is usable to generate a periodical spray puff of a liquid.

16. A method for generating a periodical motion by means of a vacuum or negative pressure, the method comprising:
providing the vacuum motor according to claim 1, wherein the working plunger and the control plunger, in a starting state, are situated in the internal space such as to be at a first distance from each other, whereby the control plunger closes the gas inlet opening and the gas outlet opening is open;

expelling gas between the working plunger and the control plunger and between the working plunger and the rear side of the internal space through the gas outlet opening;

moving the working plunger in the direction of the rear side of the internal space towards the control plunger by the pressure difference between the gas pressure exerting on the front side versus the gas pressure exerting on the rear side of the working plunger, whereby the distance between the working plunger and the control plunger decreases and the resetting element takes up and stores energy due to the motion of the working plunger;

pushing the control plunger along by the working plunger by means of the catch element or a spacer, wherein the control plunger closes the gas outlet opening due to the motion of the control plunger and the control plunger opens the gas inlet opening due to the motion of the control plunger;

flowing a compressed gas or ambient air flows through the gas inlet opening into the internal space, wherein the resetting element accelerates the working plunger in the direction of the front side of the internal space; and pulling the control plunger along by the working plunger by means of the catch element and moves the same in the direction of the front side of the internal space, preferably as soon as a first distance is reached, wherein the gas inlet opening is closed again by the reverse motion of the control plunger and the reverse motion of the control plunger opens the gas outlet opening again such that the gas between the working plunger and the rear side of the internal space is drawn out of the internal space again, wherein the second distance between working plunger and control plunger is adjusted by means of at least one spacer or the catch element and the first distance between working plunger and control plunger is adjusted by the catch element.

17. The method according to claim 16, wherein the cycle repeats upon renewed evacuation of the gas situated in the internal space between the working plunger and the rear side of the internal space.

18. A method for generating a spray puff comprising the method according to claim 16, wherein, upon a motion of the working plunger away from the rear side of the internal space, a rinsing liquid or a liquid-gas mixture is ejected from the space between the working plunger and the front side of the internal space through an ejection opening on the front side of the internal space, and further wherein, upon a motion of the working plunger towards the rear side of the internal space, a liquid or a liquid-gas mixture is pushed or pulled through a liquid supply opening into the space between the working plunger, in particular of a pump plunger, and the front side of the internal space.

19. The method according to claim 18, wherein, upon the motion of the working plunger towards the front side of the internal space, the pressure in the space between the working plunger and the front side of the internal space opens or maintains open a valve at the ejection opening and closes or maintains closed a non-return valve connected to the liquid supply opening, and further wherein, upon the motion of the working plunger towards the rear side of the internal space, the lesser pressure in the space between the working plunger and the front side of the internal space closes or maintains closed the valve on the ejection opening and opens or maintains open the non-return valve connected to the liquid supply opening.

* * * * *